(12) United States Patent
Anderson

(10) Patent No.: US 6,991,809 B2
(45) Date of Patent: Jan. 31, 2006

(54) PARTICLES WITH IMPROVED SOLUBILIZATION CAPACITY

(75) Inventor: David Anderson, Colonial Heights, VA (US)

(73) Assignee: Lyotropic Therapeutics, Inc., Ashland, VA (US)

( * ) Notice: Subject to any disclaimer, the term of this patent is extended or adjusted under 35 U.S.C. 154(b) by 393 days.

(21) Appl. No.: 10/176,112

(22) Filed: Jun. 21, 2002

(65) Prior Publication Data

US 2003/0022242 A1    Jan. 30, 2003

Related U.S. Application Data

(60) Provisional application No. 60/300,476, filed on Jun. 23, 2001.

(51) Int. Cl.
| | | |
|---|---|---|
| A61K 9/16 | (2006.01) | |
| A61K 9/14 | (2006.01) | |
| A61K 35/78 | (2006.01) | |
| B32B 27/00 | (2006.01) | |
| B32B 17/06 | (2006.01) | |

(52) U.S. Cl. .................. 424/490; 424/489; 424/491; 424/725; 424/745; 424/747; 428/402.24; 428/422; 428/426; 428/450

(58) Field of Classification Search ............. 424/489, 424/490, 491, 725, 745, 747; 428/402.24, 428/422, 426, 450
See application file for complete search history.

(56) References Cited

U.S. PATENT DOCUMENTS

| | | | |
|---|---|---|---|
| 5,154,854 A | 10/1992 | Zabotto et al. | |
| 5,531,925 A * | 7/1996 | Landh et al. ......... | 252/299.01 |
| 5,637,625 A | 6/1997 | Haynes | |
| 5,716,928 A | 2/1998 | Benet et al. | |
| 5,756,108 A | 5/1998 | Ribier et al. | |
| 5,989,583 A | 11/1999 | Amselem | |
| 6,071,524 A | 6/2000 | Ribier et al. | |
| 6,121,234 A | 9/2000 | Benet et al. | |
| 6,197,349 B1 * | 3/2001 | Westesen et al. ........... | 424/501 |
| 6,287,591 B1 | 9/2001 | Semple et al. | |
| 6,482,517 B1 * | 11/2002 | Anderson .............. | 428/402.24 |
| 6,638,621 B2 * | 10/2003 | Anderson .............. | 428/402.24 |
| 2002/0025337 A1 | 2/2002 | Illum et al. | |

FOREIGN PATENT DOCUMENTS

WO    WO 99/12640    3/1999

OTHER PUBLICATIONS

Hauss et al. from the Journal of Pharmaceutical Sciences vol. 87 No. 2 dated Feb. 1998; Lipid-based Delivery Systems for Improving Bioavalability and Lymphatic Transport of a Poorly Water-Soluble LTB Inhibitor.

Colin W. Pouton ; from the Journal of Pharmaceutical Sciences dated 2000 "Lipid formulations for oral administration of drugs: non-emulsifying, self-emulsifying and 'self microemulsifying' drug delivery systems".

Jenning et al. from the International Journal Pharmaceutics dated 2000; Characterisation of a novel solid lipid nonparticle carrier system based on binary mixtures of liquid and solid liquids.

Demiana I. Nessan, from the Journal of Pharmaceutical and Biomedical Analysis dated Feb. 10, 2001; Formulation and evaluation of itraconazole via liquid crysatl for topical delivery system.

* cited by examiner

Primary Examiner—Christopher R. Tate
(74) Attorney, Agent, or Firm—Whitham, Curtis & Christofferson, PC

(57) ABSTRACT

A particle is disclosed that comprises a first volume of hydrophobe-rich material with tunable dissolution and solubilization characteristics and a distinct second volume of nanostructured nonlamellar liquid crystalline material, said second volume containing said first domain and being capable of being in equilibrium with said first volume. Preferably, the nanostructured nonlamellar liquid crystalline material is capable of being in equilibrium with a polar solvent or a water-immiscible solvent or both.

84 Claims, 1 Drawing Sheet

PARTICLES WITH IMPROVED SOLUBILIZATION CAPACITY

This application claims priority to U.S. provisional patent application Ser. No. 60/300,476, filed Jun. 23, 2001, the complete contents of which are hereby incorporated by reference.

BACKGROUND OF THE INVENTION

1. Field of the Invention

The present invention relates to structured materials and particles and to methods of making and using them. These particles have application in the release of one or more materials into selected environments and in the absorption of one or more materials from selected environments.

2. Background of the Invention

It is desirable to provide a system for solubilizing poorly-soluble compounds, and to effectively formulate poorly-absorbed compounds whether water-soluble or not, particularly those compounds having pharmacological activity, for controlled release into, or absorption from, various environments, particularly aqueous environments.

A number of challenges to this task have not been met by existing methods of formulation. Particularly in a pharmaceutical or nutriceutical application, it is not always enough to solubilize the active or drug, even if it is in a non-toxic vehicle; the vehicle must lend itself to whatever transformation—e.g., encapsulation, granulation, enteric coating, compaction, freeze- or spray-drying—is required to arrive at the correct delivery format. For example, for pharmaceutical actives (medicaments) where the most desirable format is the pill form for oral delivery, still the most common and desirable drug format by far, most liquid solvents and even surfactant-rich phases, unless encapsulated, will often be incompatible with the simplest tablet manufacturing procedures, since these procedures were generally developed with solids and powders in mind. Yet the application of these procedures to poorly-soluble drugs, or even to drugs of moderate or high solubility, without the use of liquids or surfactants often yields a pill that achieves only a very limited bioavailability when administered. It should also be pointed out that while acidic (e.g., hydrochloride) or basic (e.g., sodium) salt forms of low-solubility drugs can often be soluble, such salts can precipitate in the body when they encounter pH conditions that deprotonate the acidic salt or protonate the basic salt.

For actives that are to be delivered by injection, solubilization of such compounds is made challenging by the very limited selection of solvents and structured liquids that are approved for injection at levels that would be required to solubilize the drug. Furthermore, water-miscible liquid excipients, e.g., ethanol, are by themselves of limited value since, even when the drug is soluble in neat ethanol, it will often precipitate upon contact with water, either diluent water for injection or in the aqueous milieu of body fluids, such as blood. In fact any (unencapsulated) delivery system containing a crucial matrix component having appreciable water solubility could partially or fully disintegrate prematurely in an aqueous environment, and lead to precipitation and/or poor absorption of the active compound.

Furthermore, delivery systems that rely on solubilization of actives in surfactant-rich (e.g., polar lipid-rich) phases, such as liposomes and lyotropic liquid crystals and liquids, are sometimes unable to solubilize appreciable loadings of active because the aliphatic chains can be incompatible with polar groups on the active compound; a great many pharmaceutical actives with low water solubility contain polar groups, in fact often 4 or more polar groups. Low drug loadings are problematic because in order to deliver a therapeutic amount of drug, large quantities of excipients must be given, increasing overall toxicity of the formulation, and often promoting low patient compliance if large, unpleasant dosage forms result; this is particularly problematic for vehicles that are themselves not well-absorbed, or do not enhance the absorption of the drug beyond the inherent enhancement due to solubilization. The particles of Landh and Larsson (U.S. Pat. No. 5,531,925) suffer from this limitation, particularly for poorly-soluble drugs but also to some extent in the case of water-soluble drugs and biopharmaceuticals (proteins, nucleic acids, and other high-MW actives). And liposomes based on lipid- or surfactant-based lamellar phases (lamellar liquid crystalline and lamellar crystalline phases) suffer from a number of well-known drawbacks and limitations, most notably unfavorable interactions with biomembranes that limit their ability to deliver their payload to cells, instability in the GI tract, lack of controllable porosity or fusogenicity, and shelf-life limitations, as well as their overall lack of success in solubilizing drugs and actives of low water solubility, making them of limited utility for both water-soluble and poorly-soluble actives. Emulsions in which lipid or surfactant monolayers, multilayers, lamellar liquid crystalline domains or lamellar crystalline domains stabilize droplets of one fluid in another similarly suffer from unfavorable interactions with biomembranes, lack of integrity particularly in the GI tract, somewhat low payload levels, poor suitability for targeting, and shelf-life limitations, and are not well suited for processing into forms that are compatible with solids-based formulations. And emulsions or droplet systems in which each droplet is surrounded by a plurality of particles of another material, all undergoing independent diffusion around the droplet (and frequently separated from one another by liquid intervening or stabilizing layers), may show good stability, but suffer from gaps between the particles that compromise the ability of the material to control the egress of active out of, or ingress of confounding factors into, the droplet.

BRIEF SUMMARY OF THE INVENTION

It is an object of the invention to provide materials and particles that are suitable for solubilizing poorly soluble and poorly-absorbed compounds, at higher loadings of active than can be obtained with comparable prior art systems, while minimizing the chance of precipitation of the active.

It is a further object of the invention to provide for this improved solubilization capability within the framework of particles based on surfactant-rich and lipid-rich phases, particularly the nanostructured nonlamellar liquid crystalline phases and more preferably the reversed nanostructured liquid crystalline phases, thus benefitting from the inherent advantages and features of these phases, such as controllable porosity, optimal milieu for biomacromolecules, compatibility with targeting strategies, amenability to various production and coating processes including those compatible with solids-based formulations, and the potential for enhancement of cell uptake and thus improved drug absorption and bioavailability. The foregoing and other objects are provided by a particle that comprises a distinct nanostructured nonlamellar liquid crystalline material and a liquid phase embedded within said distinct nanostructured nonlamellar liquid crystalline material, said liquid phase being selected from the group consisting of a hydrophobe-rich phase and a polar solvent-rich (preferably water-rich, or aqueous) phase.

It is a further object of the invention to provide materials and particles with these features and benefits in compositions that are pharmaceutically acceptable for internal administration.

The present invention thus provides a particle or material which includes a distinct nanostructured nonlamellar liquid crystalline material having a liquid phase embedded therein. The liquid phase may be oil-rich or polar solvent-rich. The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating.

The liquid phase of the particle or material may be an oil, for example, benzyl benzoate, estragole, eugenol, isoeugenol, linalool, and the essential oils of basil, bay, bois de rose (rosewood), carrot seed, clovebud, eucalyptus, ginger, grapefruit, hyssop, lemon, balsam of Peru, mugwort, myrrh gum, bitter orange, oregano, palmarosa, patchouly, peppermint, petitgrain, rosemary, santalwood oil, spearmint, thuja (cedar leaf), thyme, vanilla, or ylang ylang (cananga).

Alternatively, the liquid phase may be a polar solvent and said polar solvent such as water, glycerol, and N,N-dimethylacetamide.

The particle or material may be formulated so as to be pharmaceutically acceptable for, for example, for injection or oral delivery.

The present invention also provides a particle or material consisting essentially of a distinct nanostructured nonlamellar liquid crystalline material and at least one liquid phase embedded within the distinct nanostructured nonlamellar liquid crystalline material. The liquid phase of the particle or material may further include a bioactive oil such as santalwood, cedarwood, patchouli, peppermint, carrot see, cloves, ylang-ylang, fir needle, mugwort, oregano, Roman chamomile, eucalyptus, ginger, thuja, hyssop, or myrrh, which may for example interact strongly with biomembranes or efflux proteins so as to enhance absorption of the active. In some embodiments, the distinct nanostructured nonlamellar liquid crystalline material is a reversed phase nonlamellar liquid crystalline material such as a reversed hexagonal phase material, a reversed bicontinuous cubic phase material, a reversed discrete cubic phase material, or a reversed intermediate phase material, and may be polymerized. The particle or material may have an exterior stabilizing layer, for example, a charged moiety, a polymer, or a surfactant. The particle or material may further comprise a coating, and the coating may contain an active agent. The particle or material may be suspended in any of a wide variety of carriers compatible with a particular use of the particle or material which are well-known to those of skill in the art. For example, the carrier may be a physiologically suitable carrier for administration to a patient (e.g. a saline solution with appropriate additives such as preservatives and buffering agents that is suitable for injection, or a syrup with flavoring and/or coloring agents that is suitable for oral administration, and the like.) Alternatively, the carrier may be one that is formulated for the application of the particle or material to a targets such as plants.

The particle or material may be formulated so as to be pharmaceutically acceptable for, for example, for injection or oral delivery.

The present invention also provides a particle or material comprising a distinct nanostructured nonlamellar liquid crystalline material with a liquid phase embedded therein. The liquid phase may be an oil-rich or a polar solvent-rich liquid, and at least one active agent may be dissolved or dispersed in the liquid phase, or in the distinct nanostructured nonlamellar liquid crystalline material. The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating. The coating may also contain an active agent.

The liquid phase may be an oil such as benzyl benzoate, estragole, eugenol, isoeugenol, linalool, and the essential oils of basil, bay, bois de rose (rosewood), carrot seed, clovebud, eucalyptus, ginger, grapefruit, hyssop, lemon, balsam of Peru, mugwort, myrrh gum, bitter orange, oregano, palmarosa, patchouly, peppermint, petitgrain, rosemary, santalwood oil, spearmint, thuja (cedar leaf), thyme, vanilla, and ylang ylang (cananga). Alternatively, the liquid phase may be a polar solvent such as water, glycerol, and N,N-dimethylacetamide.

The active agents contained in the particle or material may be, for example, pigments, fillers, texturizing agents, opacifiers, non-wovens, chelating agents, polymerization catalysts, explosives, and propellants. In a preferred embodiment, the active agent is a bioactive agent among such as agents as targeting moieties, membrane proteins, absorption agents, fertilizer, pesticides, nucleic acids, antineoplastic agents, antibiotics, antimetabolites, proteins, hormones, hormone analogs, antineoplastic adjuncts, radiation sources, pheromones, growth regulators, herbicides, taste modifiers, vaccines, radionuclides, insecticides, proteins, and medicaments. The term medicaments includes but is not limited to organic or inorganic moieties also typically referred to as "drugs", examples of which include but are not limited to aspirin, ibuprofen, and the like.

In preferred embodiments, the active agent is of low solubility in lipid-water systems.

In yet other preferred embodiments, the active agent(s) may be taxanes, paclitaxel, vancomycin, cephalosporins, ceftriaxone, dantrolene, camptothecins, platinum anticancer compounds, and cisplatin.

The particle or material may be formulated so as to be pharmaceutically acceptable, for example, for injection or for oral delivery.

The present invention also provides a composition which includes a carrier; and a particle or material dispersed within the carrier. The particle or material includes a distinct nanostructured nonlamellar liquid crystalline material with a liquid phase (e.g. an oil or a polar solvent) embedded therein. The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating. The coating may also contain an active agent. The liquid phase may be an oil such as benzyl benzoate, estragole, eugenol, isoeugenol, linalool, and the essential oils of basil, bay, bois de rose (rosewood), carrot seed, clovebud, eucalyptus, ginger, grapefruit, hyssop, lemon, balsam of Peru, mugwort, myrrh gum, bitter orange, oregano, palmarosa, patchouly, peppermint, petitgrain, rosemary, santalwood oil, spearmint, thuja (cedar leaf), thyme, vanilla, and ylang ylang (cananga). Alternatively, the liquid phase may be rich in a polar solvent such as, for example, water, glycerol, and N,N-dimethylacetamide.

At least one active agent may be dissolved or dispersed in the liquid phase and/or in the distinct nanostructured nonlamellar liquid crystalline material. For example, the active agents may be pigments, fillers, texturizing agents, opacifiers, non-wovens, chelating agents, polymerization catalysts, explosives, and propellants. In a preferred embodiment, the active agents are bioactive agents such as targeting moieties, membrane proteins, absorption agents, fertilizer, pesticides, nucleic acids, antineoplastic agents, antibiotics, antimetabolites, proteins, hormones, hormone analogs, antineoplastic adjuncts, radiation sources, pheromones, growth regulators, herbicides, taste modifiers, vaccines, radionuclides, insecticides, proteins, and medicaments, which are defined above.

The particle or material may be formulated so as to be pharmaceutically acceptable, for example, for injection or for oral delivery.

In alternative embodiments of the invention:
1) the liquid phase of the particle or material is an oil and the carrier is hydrophobic;
2) the liquid phase is polar-solvent rich and the carrier is hydrophobic;
3) the liquid phase is oil-rich and the carrier is hydrophilic; and
4) the liquid phase is a polar solvent and said carrier is hydrophilic.

The invention further provides a method of delivering at least one bioactive agent to a targeted entity, comprising the steps of 1) providing a particle or material comprising a distinct nanostructured nonlamellar liquid crystalline material. a liquid phase embedded therein, (the liquid phase being an oil or aqueous phase), and wherein the at least one bioactive agent is dissolved or dispersed in the liquid phase, or in the distinct nanostructured nonlamellar liquid crystalline material, or both; and 2) administering the particle or material to the targeted entity.

The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating. The coating may also contain an active agent.

The targeted entity may be a patient in need of the at least one bioactive agent, and may be an animal or human.

Administration may be carried out by a method such as parenteral, intravenous, oral, transdermal, buccal, rectal, otic, occular, nasal, and sublingual.

The bioactive agents may be targeting moieties, membrane proteins, absorption agents, fertilizer, pesticides, nucleic acids (particularly DNA), antineoplastic agents, antibiotics, antimetabolites, proteins, hormones, hormone analogs, antineoplastic adjuncts, radiation sources, pheromones, growth regulators, pesticides, herbicides, taste modifiers, vaccines, radionuclides, insecticides, proteins, medicaments and P-glycoprotein inhibitors.

In one embodiment, the targeted entity is a plant. In this case, administration may be carried out by applying the particle or material to leaves or to roots of the plant, and the bioactive agent may be, for example, fertilizer, pesticides, nucleic acid, protein, growth factor, and hormone.

For purposes of administration, the particle or material may be suspended in a carrier as described above.

The particle or material may be formulated so as to be pharmaceutically acceptable, for example, for injection or for oral delivery.

The present invention also provides a method for the controlled-release delivery of at least one active agent to a medium (e.g. the body fluid of an animal). The method includes the steps of 1) providing a particle or material comprising a distinct nanostructured nonlamellar liquid crystalline material with a liquid phase (an oil and a polar solvent) embedded therein, and at least one active agent is dissolved or dispersed in the liquid phase; and 2) disposing said particle or material in the medium, so that the step of disposing results in the controlled release of the al least one active agent from the liquid phase through the distinct nanostructured nonlamellar liquid crystalline material and into the medium.

The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating. The coating may also contain an active agent.

Further, the distinct nanostructured nonlamellar liquid crystalline material may contain at least one active agent dissolved or dispersed therein.

The particle or material may be formulated so as to be pharmaceutically acceptable, for example, for injection or for oral delivery. The controlled release of the active may be mediated by pore size, or, alternatively by an environmental trigger such as pH, temperature, pressure, surfactant, an enzyme, ionic strength, dilution, chemical reaction, complexation, irradiation, or shear.

The present invention also provides a method for the absorption of a compound of interest from a medium, comprising the steps of 1) providing a particle or material comprising a distinct nanostructured nonlamellar liquid crystalline material and a liquid phase (an oil or a polar solvent) embedded therein, and wherein the compound of interest is soluble in the liquid phase; and 2) disposing the particle or material in the medium, such the compound of interest is absorbed from medium through the distinct nanostructured nonlamellar liquid crystalline material and into the liquid phase.

The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating. The coating may also contain an active agent.

The present invention also provides a method of providing to a patient in need thereof a poorly soluble compound having pharmacological activity. The method includes the step of administering to the patient a composition comprising a particle or material comprising a distinct nanostructured nonlamellar liquid crystalline material with a liquid phase (oil or aqueous phase) embedded therein, in which the poorly soluble compound is dissolved or dispersed in the liquid phase.

The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating. The coating may also contain an active agent.

The distinct nanostructured nonlamellar liquid crystalline material contains at least one active agent dissolved or dispersed therein.

The particle or material may be formulated so as to be pharmaceutically acceptable, for example, for injection or for oral delivery.

The present invention also provides a composition comprising 1) a carrier, 2) a first particle or material which includes a distinct nanostructured nonlamellar liquid crystalline material with a first liquid phase (an oil or aqueous phase) embedded therein, and a first active agent dissolved or solubilized in the first liquid phase; and 3) a second particle or material comprising a distinct nanostructured nonlamellar liquid crystalline material with a second liquid phase (an oil or aqueous phase) embedded therein, and a second active agent dissolved or solubilized in the second liquid phase. The first and second liquid phases may be the same or different. The first and second active agents may be the same or different. The first and second active agents may be bioactive agents.

The present invention also provides a particle or material comprising 1) a distinct nanostructured nonlamellar liquid crystalline material with a first liquid phase embedded within a first region thereof, and a second liquid phase embedded within a second region of the distinct nanostructured nonlamellar liquid crystalline material. The first and second liquid phases may be an oil or a polar solvent, and the first and second liquid phases have at least one active agent dissolved or dispersed therein. The first and second liquid phases may be the same or different.

The active agent(s) dissolved or dispersed in the first liquid phase may different than the active agent(s) dissolved or dispersed in the second liquid phase.

The active agent(s) may be released from the particle or material in response to a stimulus such as, for example, time, pH, temperature, pressure, surfactant, an enzyme, ionic strength, dilution, chemical reaction, complexation, irradiation, or shear. The active agents may interact with each other upon release from the particle or material.

The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating. The coating may also contain an active agent.

The liquid phase may be an oil such as benzyl benzoate, estragole, eugenol, isoeugenol, linalool, and the essential oils of basil, bay, bois de rose (rosewood), carrot seed, clovebud, eucalyptus, ginger, grapefruit, hyssop, lemon, balsam of Peru, mugwort, myrrh gum, bitter orange, oregano, palmarosa, patchouly, peppermint, petitgrain, rosemary, santalwood oil, spearmint, thuja (cedar leaf), thyme, vanilla, or ylang ylang (cananga). The liquid phase may be a polar solvent such as water, glycerol, and N,N-dimethylacetamide.

The active agent(s) may be pigments, fillers, texturizing agents, opacifiers, non-wovens, chelating agents, polymerization catalysts, explosives, and propellants. the active agent(s) may be bioactive agents such as targeting moieties, membrane proteins, absorption agents, fertilizer, pesticides, nucleic acids, antineoplastic agents, antibiotics, antimetabolites, proteins, hormones, hormone analogs, antineoplastic adjuncts, radiation sources, pheromones, growth regulators, pesticides, herbicides, taste modifiers, vaccines, radionuclides, insecticides, proteins, and medicaments. In one embodiments, the bioactive agent dissolved or dispersed in the first liquid phase is a nucleic acid and the bioactive agent dissolved or dispersed in the second liquid phase is Lipofectamine®.

The distinct nanostructured nonlamellar liquid crystalline material may contain at least one active agent dissolved or dispersed therein.

The particle or material may be formulated so as to be pharmaceutically acceptable, for example, for injection or for oral delivery.

The present invention also provides a method of making a particle or material comprising the steps of 1) providing a hydrophobe-rich material which is tuned to exhibit specified solubilization characteristics and a distinct nanostructured nonlamellar liquid crystalline material; and 2) combining the hydrophobe-rich material and the distinct nanostructured nonlamellar liquid crystalline material to form a particle or material in which the hydrophobe-rich material is contained within and is in thermodynamic equilibrium with the distinct nanostructured nonlamellar liquid crystalline material.

The present invention also provides a method of making a particle or material comprising the steps of 1) providing a polar solvent-rich material which is tuned to exhibit specified solubilization characteristics and a distinct nanostructured nonlamellar liquid crystalline material; and 2) combining the polar solvent-rich material and the distinct nanostructured nonlamellar liquid crystalline material to form a particle or material in which the polar solvent-rich material is contained within and is in thermodynamic equilibrium with the distinct nanostructured nonlamellar liquid crystalline material.

The present invention also provides a method of making a particle or material comprising the steps of 1) tuning a hydrophobe-rich material or a polar solvent-rich material to exhibit specified solubilization characteristics, thus forming a tuned hydrophobe-rich material or a tuned polar solvent-rich material, and 2) combining the tuned hydrophobe-rich material or the tuned polar solvent-rich material with a distinct nanostructured nonlamellar liquid crystalline material to form a particle or material. The tuned hydrophobe-rich material or the tuned polar solvent-rich material is contained within and is in thermodynamic equilibrium with the distinct nanostructured nonlamellar liquid crystalline material in the particle or material.

The distinct nanostructured nonlamellar liquid crystalline material may be a reversed phase nonlamellar liquid crystalline material, for example, a reversed hexagonal phase material, a reversed bicontinuous cubic phase material, a reversed discrete cubic phase material, or a reversed intermediate phase material, and may be polymerized. The particle or material may include an exterior stabilizing layer such as a charged moiety, a polymer, or a surfactant. Further, the particle or material may have a coating. The coating may also contain an active agent.

The tuned hydrophobe-rich material or the tuned polar solvent-rich material may include at least one active agent such as pigments, fillers, texturizing agents, opacifiers, nonwovens, chelating agents, polymerization catalysts, explosives, and propellants. The active agent(s) may be bioactive agent(s) such as targeting moieties, membrane proteins, absorption agents, fertilizer, pesticides, nucleic acids, antineoplastic agents, antibiotics, antimetabolites, proteins, hormones, hormone analogs, antineoplastic adjuncts, radiation sources, pheromones, growth regulators, herbicides, taste modifiers, vaccines, radionuclides, insecticides, proteins, and medicaments.

The distinct nanostructured nonlamellar liquid crystalline material may contain at least one active agent dissolved or dispersed therein.

The particle or material may be formulated so as to be pharmaceutically acceptable, for example, for injection or for oral delivery.

In the context of the present invention, bioactive agents may, for example, be nucleic acids. The term "nucleic acids" includes but is not limited to such species as single-strand and double-strand DNA, RNA and hybrids of DNA and RNA, and also complexes of nucleic acids with proteins or other suitable substances. The bioactive agents may also be proteins (for example, enzymes, antibodies, and the like) or polypeptides, and peptide fragments of proteins and polypeptides, or oligosaccharides and polysaccharides Further, these bioactive agents may be combined or complexed.

The present invention also provides a method of making a particle comprising a distinct nanostructured nonlamellar liquid crystalline material and a hydrophobe-rich liquid phase embedded within the distinct nanostructured nonlamellar liquid crystalline material. The method comprises the steps of i. determining a composition that yields an equilibrium between said nanostructured nonlamellar liquid crystalline phase and said hydrophobe-rich liquid phase, and ii. contacting said nanostructured nonlamellar liquid crystalline phase and said liquid phase with a polar solvent-rich liquid and applying energy to disperse said nanostructured nonlamellar liquid crystalline phase and said hydrophobe-rich liquid phase into said polar solvent-rich liquid.

The present invention also provides a method of making a particle comprising a distinct nanostructured nonlamellar liquid crystalline material and a polar solvent-rich liquid phase embedded within said distinct nanostructured nonlamellar liquid crystalline material, comprising the steps of i. determining a composition that yields an equilibrium between said nanostructured nonlamellar liquid crystalline phase and said polar solvent-rich liquid phase, and ii. contacting said nanostructured nonlamellar liquid crystalline phase and said liquid phase with a hydrophobe-rich liquid and applying energy to disperse said nanostructured nonlamellar liquid crystalline phase and said polar solvent-rich liquid phase into said hydrophobe-rich liquid.

The present invention also provides a method of making a particle comprising a distinct nanostructured nonlamellar liquid crystalline material and a hydrophobe-rich liquid phase embedded within said distinct nanostructured nonlamellar liquid crystalline material, comprising the steps of i. determining a composition that yields an equilibrium between said nanostructured nonlamellar liquid crystalline phase, said hydrophobe-rich liquid phase, and a polar solvent-rich liquid, and ii. contacting said nanostructured nonlamellar liquid crystalline phase and said hydrophobe-rich liquid phase with said polar solvent-rich liquid and applying energy to disperse the said nanostructured nonlamellar liquid crystalline phase and said hydrophobe-rich liquid phase into said polar solvent-rich liquid.

The present invention also provides a method of making a particle comprising a distinct nanostructured nonlamellar liquid crystalline material and a polar solvent-rich liquid phase embedded within said distinct nanostructured nonlamellar liquid crystalline material, comprising the steps of i. determining a composition that yields an equilibrium between said nanostructured nonlamellar liquid crystalline phase, said polar solvent-rich liquid phase, and a hydrophobe-rich liquid phase, and ii. contacting said nanostructured nonlamellar liquid crystalline phase and said polar solvent-rich liquid phase with said hydrophobe-rich liquid and applying energy to disperse the said nanostructured nonlamellar liquid crystalline phase and said polar solvent-rich liquid phase into said hydrophobe-rich liquid.

The present invention also provides a method of making a material comprising a distinct nanostructured nonlamellar liquid crystalline material and a liquid phase embedded within said distinct nanostructured nonlamellar liquid crystalline material, said liquid phase being selected from the group consisting of an oil and a polar solvent, comprising the steps of i. determining a composition that yields an equilibrium between said nanostructured nonlamellar liquid crystalline phase and said liquid phase, and ii. spraying or otherwise dispersing in air a material of this composition.

The present invention also provides a method of making a material comprising a distinct nanostructured nonlamellar liquid crystalline material and a liquid phase embedded within said distinct nanostructured nonlamellar liquid crystalline material, said liquid phase being selected from the group consisting of an oil and a polar solvent, comprising the steps of i. determining a composition that yields an equilibrium between said nanostructured nonlamellar liquid crystalline phase and said liquid phase ii. liquifying a material of said composition by heating, or adding volatile solvent, and iii. spraying or otherwise dispersing in air said liquified material.

The present invention also provides a method of making a material comprising a distinct nanostructured nonlamellar liquid crystalline material and a hydrophobe-rich liquid phase embedded within said distinct nanostructured nonlamellar liquid crystalline material, comprising the steps of i. determining a composition that yields an equilibrium between said nanostructured nonlamellar liquid crystalline phase and said hydrophobe-rich liquid phase, and ii. contacting said nanostructured nonlamellar liquid crystalline phase with said liquid phase and applying energy to disperse said hydrophobe-rich liquid phase into said nanostructured nonlamellar liquid crystalline phase.

The present invention also provides a method of making a material comprising a distinct nanostructured nonlamellar liquid crystalline material and a polar solvent-rich liquid phase embedded within said distinct nanostructured nonlamellar liquid crystalline material, comprising the steps of i. determining a composition that yields an equilibrium between said nanostructured nonlamellar liquid crystalline phase and said polar solvent-rich liquid phase, and ii. contacting said nanostructured nonlamellar liquid crystalline phase with said polar solvent-rich liquid phase and applying energy to disperse said polar solvent-rich liquid phase into said nanostructured nonlamellar liquid crystalline phase.

DESCRIPTION OF THE PREFERRED EMBODIMENTS

Figure 1:
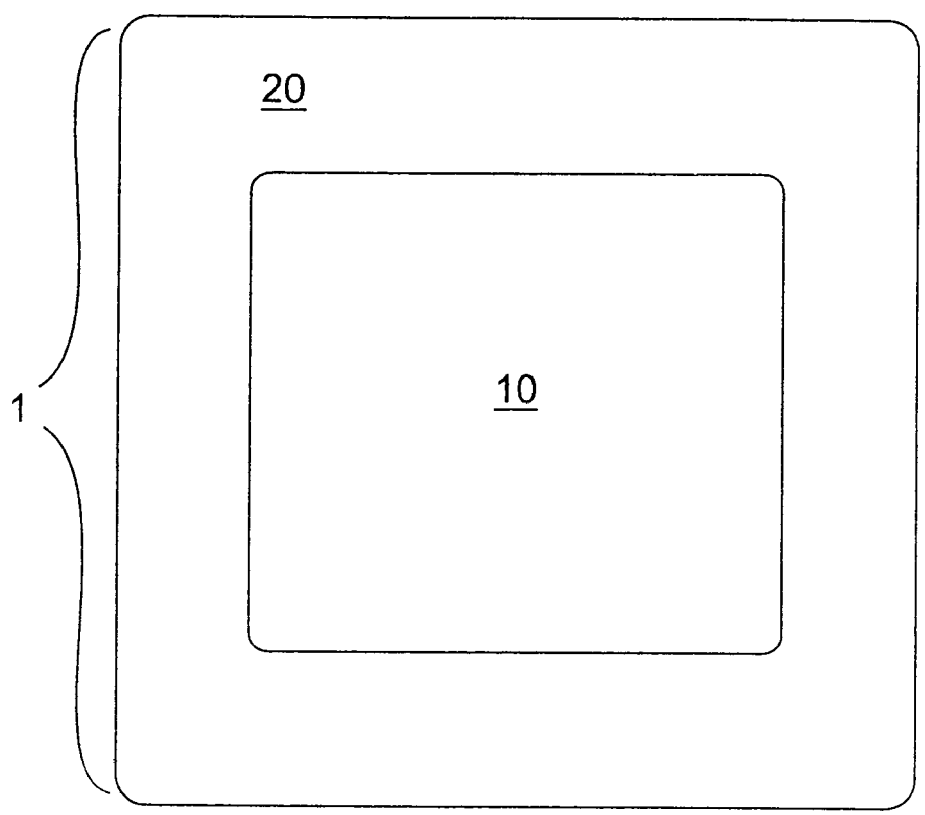
FIG. 1 is a graphic representation, in section, illustrating a particle of the present invention.

As illustrated in FIG. 1, a particle 1 of the present invention comprises a first volume 10 of a liquid phase and a distinct second volume 20 of nanostructured nonlamellar liquid crystalline material, the second volume containing and enclosing said first volume, and being in equilibrium with the liquid phase of the first volume. Preferably, the nanostructured nonlamellar liquid crystalline material is also capable of being in equilibrium with a liquid of opposite polarity characteristics from those of the first volume, that is, a polar solvent in the case where the first volume is a hydrophobe-rich liquid phase, or a hydrophobic solvent in the case where the first volume is a polar solvent-rich liquid phase.

The particles of the present invention obviate many or most of the limitations of prior particles in a robust manner. The present invention contemplates a range of low-toxicity or non-toxic compositions that form nanostructured nonlamellar liquid crystalline phases, such as reversed hexagonal and reversed cubic phases that exist not only in equilibrium with water (or dilute aqueous solution), but also simultaneously in equilibrium with hydrophobe-rich liquid phases which can solubilize substantial loadings of poorly-water-soluble materials, such as poorly-water-soluble drugs. When appropriately formulated, these systems can be made to form materials or microdroplet systems in which the drug is solubilized in hydrophobe-rich liquid pockets (the first volume 10), and each pocket is enclosed by a nanostructured nonlamellar liquid crystalline phase material (the second volume 20), preferably a liquid crystalline phase and more preferably a reversed liquid crystalline phase; in many embodiments such microdroplets can be, in turn, dispersible in a continuous polar solvent-rich (preferably water-rich) medium. Alternatively, such systems can be formulated so as to form materials or microdroplet systems in which the drug is solubilized in polar solvent-rich (typically water-rich) liquid pockets, and each pocket is enclosed by a nanostructured nonlamellar liquid crystalline phase material, preferably a liquid crystalline phase and more preferably a reversed liquid crystalline phase; in many embodiments such microdroplets can be, in turn, dispersible in a continuous hydrophobe-rich medium.

While the dominant polar solvent, in the case where the first volume is polar solvent-rich, is typically water, there are notable situations in which other solvents or solvent combinations, are particularly advantageous. For example, in the case of the solubilization of an active that is of low solubility in water as well as in pharmaceutically-acceptable hydrophobes, e.g., dantrolene or other hydantoin-containing molecule, a judicious choice could be a combination of N,N-dimethylacetamide and glycerol. This combination can in many cases yield high loadings of the active and yet be compatible with the existence of liquid crystals-that is, the liquid crystals do not liquify from the presence of the dimethylacetamide, provided the ratio of glycerol to dimethylacetamide is high enough; generally, a ratio of roughly 3:1 glycerol:dimethylacetamide is a good ratio.

The second volume 20 encloses the first volume 10, but this is not intended to be limited to meaning that the second volume 20 is the most exterior material of the particle 1. In particular, a particularly useful embodiment is one in which there is a solid coating material at the outer surface of the second volume 20.

Nanostructured liquid crystalline phases of the reversed type—namely reversed cubic, reversed intermediate, and reversed hexagonal phases—can be of very low solubility in water, meaning that they maintain their integrity as vehicles upon entry into the body thus avoiding drug precipitation, and show a great deal of promise in fields such as controlled-release drug delivery. In work motivated by the amphiphilic nature and porous nanostructures of these materials, which could lead to very advantageous interactions with biomembranes—much more intimate than in the case of liposomes—and by the high viscosities of these phases which can be an important aid in processing, a number of techniques have been developed for encapsulating such phases, with those of the present author being of particular importance in the present context. See U.S. patent application Ser. No. 09/297,997 filed Aug. 16, 2000 (notice of allowance issued and issue fee paid, which is incorporated in its entirely by way of reference). Nanostructured nonlamellar liquid crystalline phase materials possess unique properties that are not only important in making possible the easy production of particles according to the present invention, but also yield highly desirable absorption, stability, adhesion, and presentation properties as well as other capabilities in the final particles of the present invention.

The solubilization of an active, or preferably bioactive, compound in a nonlamellar liquid crystalline matrix is fundamentally a very promising approach from the point of view of drug-delivery, because absorption of the drug by lipid bilayers of the body, or passage across absorption barriers comprising lipid bilayers, can be facilitated by more intimate and favorable interactions between these matrices and bilayers of the body, particularly in the case of reversed cubic and hexagonal phases. In contrast, matrices based on lamellar phases and materials, such as liposomes, generally rely on processes such as endocytosis or pinocytosis for interacting with cells, which are not only slow and inefficient but can result in an intact matrix trapped inside an endosome. Furthermore, the solubilization of difficultly-soluble pharmaceutical actives in liposomes has not met with great success.

The current author has demonstrated the relationship between curvature properties of lipids and their tendency to promote porosity in bilayers, and their tendency to form reversed cubic and other reversed phases including L3 and reversed hexagonal phases. See Anderson D. M., Wennerstrom, H. and Olsson, U., J. Phys. Chem. 1989, 93:4532–4542. The tendency to induce or form porous microstructures is viewed in the present context as being advantageous with respect to drug-delivery, in that it promotes the integration of the administered lipidic microparticles with biomembranes that otherwise form barriers to absorption, in contrast with lamellar lipidic structures such as liposomes which show low curvature, and little or no porosity, and do not ordinarily show strong tendencies to integrate with biomembranes.

Nanostructured nonlamellar liquid crystalline phases are synthetic or semisynthetic materials which provide pure, well-characterized, easily produced, often inexpensive matrices that have the following desirable properties:

a) versatility in chemical systems forming nanostructured nonlamellar liquid crystalline phases, ranging from biological lipids that are ideal for biomolecules, to hardy fluorosurfactants, to glycolipids that bind bacteria, to surfactants with ionic or reactive groups, etc.; this provides for applicability over a wide range of conditions and uses;

b) the unsurpassed ability of nanostructured nonlamellar liquid crystalline phases to provide the biochemical environment that preserves the structure and function of bioactive molecules such as proteins or peptides; in particular, the poresizes of cubic and hexagonal phases generally occur over the range 1–20 nm, the range corresponding to the effective sizes of proteins, nucleic acids, and other biomacromolecules, and the geometric fit permits intimate interactions between the polar and apolar portions of these macromolecules with polar and apolar domains of the liquid crystals, particularly the reversed cubic phases;

c) true thermodynamic stability, which controls instabilities common with other vehicles, such as precipitation of active agents, collapse of particles into bulk phases (e.g., with liposomes), nonreproducibility, etc.;

d) the presence of a porespace with preselectable pore size in the nanometer range also facilitates further control of the release kinetics, particularly in the release of proteins and other biomacromolecules, as well as effecting the exclusion of problematic proteins such as proteases, nucleases, strongly adsorbing proteins (such as albumin), etc.;

e) the high viscosities of the nonlamellar liquid crystalline phases, especially the reversed hexagonal and cubic phases, but also the intermediate and hexagonal in many cases, mean that these phases retain their integrity to a greater degree under shear forces as occur in applications and production processes such as coating processes; and, f) the reversed liquid crystalline phases in particular have a pronounced ability to promote absorption of active across cell membranes (e.g., intestinal epithelial cells), in part by virtue of substantial monolayer curvature, porosity, and fusogenic potential.

Particles 1 of the present invention may be from 0.1 micron to 30 microns in mean caliper diameter or even larger, and preferably from about 0.2 micron to about 5 microns in mean caliper diameter. The particle 1 may also be provided with a stabilizing layer on its exterior, i.e., outside the second volume 20, as desired, such as a charged moiety, polymer, or surfactant-rich layer to prevent agglomeration of coated particles 1. For example, the present inventor has disclosed methods for encapsulating particles of liquid crystals, preferably reversed liquid crystalline phases, in solid coatings; see U.S. patent application Ser. No. 09/297,997 filed Aug. 16, 2000 (notice of allowance issued and issue fee paid). Also, U.S. Pat. No. 5,531,925 describes the production of particles with reversed cubic and hexagonal phase interiors and lamellar crystalline surface phases. The methods described in these patents apply equally well to particles of the instant invention, as will be recognized by someone with skill in the art, and can be applied to produce particles of the instant invention with solid coatings that can comprise crystalline, amorphous, or semi-crystalline material. Particles of the instant invention, with a coating comprising a solid material that can be crystalline, amorphous, or semi-crystalline, may be a particularly powerful embodiment of the instant invention. One such embodiment is exemplified in Example 11 herein with one method of producing it described. Whether coated or uncoated, particles (and more generally, materials) of the instant invention can far exceed the capabilities of prior art particles and materials, particularly in terms of the amount of payload that can be solubilized per unit mass (or volume) of total particle, which is crucial in reducing the total quantity of excipients required for the administration of a therapeutic amount of active (typically a drug); this is amplified further by the absorption-enhancing capabilities of certain liquid crystals, so that particles of this invention can excel at reducing the total quantity of excipients required for the absorption, by the body, of a therapeutic amount of active.

Macroscopic materials can be produced within the scope of this invention. Thus, using the same equilibrium between a liquid phase and nonlamellar liquid crystalline phase as used in an embodiment producing particles of the instant invention, one can produce in a number ways materials of macroscopic dimensions in which either microscopic or macroscopic droplets of the liquid phase are enclosed by the liquid crystalline phase. A person with skill in the art will recognize that the much higher viscosities of the nonlamellar liquid crystalline phases, as compared to those of lamellar phases, make such an approach more sensible and robust in the case of nonlamellar liquid crystals.

The particles 1 of the present invention have application in a variety of modalities of use. The particle 1 may release one or more materials, such as active agents, disposed in the first volume into a selected environment. In a preferred embodiment, an additional material, such as an active agent, may be disposed within the first volume 10 for release into a selected environment, through the intermediation of the second volume 20. Alternatively, one or more compounds can be absorbed from the environment into the core 10 through the second volume.

The second volume is a. thermodynamically stable, b. nanostructured, c. a non-lamellar liquid crystalline phase and d. capable of being in equilibrium with the first volume.

Some definitions follow.

Hydrophobe: The term "hydrophobe" as used herein is a compound that has a relatively low solubility in water, wherein low solubility means less than about 40 mg/ml, and more preferably less than about 10 mg/ml, has a relatively high octanol-water coefficient (greater than or equal to about 10, preferably greater than about 100), and does not satisfy the definition of a surfactant (see below).

Hydrophobe-rich: The term "hydrophobe-rich" as used herein is used in the sense that a liquid or liquid mixture is hydrophobe-rich if it contains a high volume fraction of hydrophobe(s), at least 50%, and that the hydrophobic domains are continuous. (Note that hydrophobe-continuous, or oil-continuous, does not necessarily imply that water is discontinuous; certain liquid and liquid crystalline phases are "bicontinuous", meaning that both oil and water are continuous simultaneously).

Tunable: The term "tunable" as used herein is used in the sense that a liquid has tunable solubilization characteristics if its chemical composition can be chosen or adjusted so as to achieve a sufficient, preferably high, solubility of active drug, especially for a particular drug of interest, wherein sufficient solubility means that less than about 10 grams, or preferably less than about 3 grams, of the liquid are required to solubilize one therapeutic dose of the drug, at body temperature. It follows that the term "tuning" is the act of performing this choice or adjustment.

Dissolution: The term "dissolution" as used herein is used in the sense that dissolution of a compound refers to the action of achieving solubilization of the compound, in simple terms, dissolving the compound.

Solubilization: The term "solubilization" as used herein is used in the sense that a compound (usually a drug) is solubilized in a liquid if the compound and liquid form a single phase, in the true thermodynamic sense of the term, and thus complete solubilization of the compound precludes the possibility of solid, crystalline particles of the compound coexisting with the liquid.

Domain: The term "domain" as used herein is used in the sense that a domain is a volume within a material throughout which the chemical microenvironment is substantially uniform with respect to a particular property of interest, which is composition-related and often, in the present context, the property of being hydrophobic; by substantially uniform is meant that variations in this property of interest within that volume are small relative to the difference in this property between this volume and the space immediately adjacent to that volume.

Difficultly soluble or poorly soluble (and other terms of similar import): In the context of the present invention, a drug is difficultly soluble if a therapeutic amount of the drug cannot be dissolved in less than about 100 ml of water.

Low solubility in lipid-water systems: an active will be said to be of low solubility in lipid-water systems if it requires more than 2 grams of a 60:40 mixture of monoolein to water in order to solubilize a therapeutic amount of active. In the absence of an active, this mixture forms a reversed cubic phase, though the addition of active could change this. The presence of water and of lipid, and an extensive polar-apolar interface, in this mixture is capable of solubilizing a number of actives at levels that are sufficiently high, so that solubilization in this or another lipid-water system would not require inordinate levels of excipients. However, if more than 2 grams of this mixture are required, then this simplistic approach will encounted major problems: the toxicity of the vehicle will rise in importance, and patient compliance would be expected to be problematic since several large "horse-pills" would be required for an oral dose, for example. In such a case, the instant invention provides a means by which to greatly improve the solubilization of the drug and reduce the level of excipients and dosage volume.

Nanostructured: The terms "nanostructure" or "nanostructured" as used herein in the context of the structure of a material refer to materials the building blocks of which have a size that is on the order of nanometers ($10^{-9}$ meter) or tens of nanometers ($10 \times 10^{-9}$ meter.) Generally speaking, any material that contains domains or particles 1 to 100 nm (nanometers) across, or layers or filaments of that thickness, can be considered a nanostructured material. (See also Dagani, R., "Nanostructured Materials Promise to Advance Range of Technologies," Nov. 23, 1992 C&E News 18 (1992).) The term is meant to exclude so-called "ceramic glasses" which are crystalline materials in which the crystallite size is so small that one may not observe peaks in wide-angle x-ray diffraction and which some physicists may refer to as nanostructured materials; the nanostructured nonlamellar liquid crystalline phases that are defined herein are characterized by nanoscale domains which are clearly distinguished from neighboring domains by large differences in local chemical composition, and do not include materials in which neighboring domains have essentially the same local chemical composition and differ only in lattice orientation. Thus, by the term 'domain' as used herein it is meant a spatial region which is characterized by a particular chemical makeup, which is clearly distinguishable from that of neighboring domains; often such a domain is hydrophilic (hydrophobic) which contrasts with the hydrophobicity (hydrophilicity) of neighboring domains; in the context of this invention the characteristic size of these domains is in the nanometer range. (The term 'microdomain' is often used to indicate domains whose size range is micron or nanometer scale.)

Polar: polar compounds (such as water) and polar moieties (such as the charged head groups on ionic surfactants or on lipids) are water-loving, or hydrophilic; "polar" and "hydrophilic" in the context of the present invention are essentially synonymous. In terms of solvents, water is not the only polar solvent. Others of importance in the context of the present invention are: glycerol, ethylene glycol, formamide, N-methyl formamide, dimethylformamide, ethylammonium nitrate, and polyethylene glycol. Note that one of these (polyethylene glycol) is actually a polymer, thereby illustrating the range of possibilities. At sufficiently low molecular weights, polyethylene glycol (PEG) is a liquid, and although PEG has not been extensively studied as a polar solvent in combination with surfactants, it has been found that PEG does form liquid crystalline phases in combination with, for example, surfactants such as BRIJ-type surfactants, which are nonionic surfactants with PEG head groups ether-linked to alkane chains. More generally, in terms of polar groups in hydrophilic and amphiphilic molecules (including but not limited to polar solvents and surfactants), a number of polar groups are tabulated below, in the discussion of which polar groups are operative as surfactant head groups and which are not.

Apolar: Apolar (or hydrophobic, or alternatively "lipophilic") compounds include not only the paraffinic/hydrocarbon/alkane chains of surfactants, but also modifications of them, such as perfluorinated alkanes, as well as other hydrophobic groups, such as the fused-ring structure in cholic acid as found in bile salt surfactants, or phenyl groups as form a portion of the apolar group in TRITON-type surfactants, and oligomer and polymer chains that run the gamut from polyethylene (which represents a long alkane chain) to hydrophobic polymers, such as hydrophobic polypeptide chains in novel peptide-based surfactants that have been investigated. A listing of some apolar groups and compounds is given below, in the discussion of useful components of the nanostructured phase interior.

Amphiphile: an amphiphile can be defined as a compound that contains both a hydrophilic and a lipophilic group. See D. H. Everett, Pure and Applied Chemistry, vol. 31, no. 6, p. 611, 1972. It is important to note that not every amphiphile is a surfactant. For example, butanol is an amphiphile, since the butyl group is lipophilic and the hydroxyl group hydrophilic, but it is not a surfactant since it does not satisfy the definition, given below. There exist a great many amphiphilic molecules possessing functional groups which are highly polar and hydrated to a measurable degree, yet which fail to display surfactant behavior. See R. Laughlin, Advances in liquid crystals, vol. 3, p. 41, 1978.

Surfactant: A surfactant is an amphiphile that possesses two additional properties. First, it significantly modifies the interfacial physics of the aqueous phase (at not only the air-water but also the oil-water and solid-water interfaces) at unusually low concentrations compared to nonsurfactants. Second, surfactant molecules associate reversibly with each other (and with numerous other molecules) to a highly exaggerated degree to form thermodynamically stable, macroscopically one-phase, solutions of aggregates or micelles. Micelles are typically composed of many surfactant molecules (10's to 1000's) and possess colloidal dimensions. See R. Laughlin, Advances in liquid crystals, vol. 3, p. 41, 1978. Lipids, and polar lipids in particular, often are considered as surfactants for the purposes of discussion herein, although the term 'lipid' is normally used to indicate that they belong to a subclass of surfactants which have slightly different characteristics than compounds which are normally called surfactants in everyday discussion. Two characteristics which frequently, though not always, are possessed by lipids are, first, they are often of biological origin, and second, they tend to be more soluble in oils and fats than in water. Indeed, many compounds referred to as lipids have extremely low solubilities in water, and thus the presence of a hydrophobic solvent may be necessary in order for the interfacial tension-reducing properties and reversible self-association to be most clearly evidenced, for lipids which are indeed surfactants. Thus, for example, such a compound will strongly reduce the interfacial tension between oil and water at low concentrations, even though extremely low solubility in water might make observation of surface tension reduction in the aqueous system difficult; similarly, the addition of a hydrophobic solvent to a lipid-water system might make the determination of self-association into nanostructured nonlamellar liquid crystalline phases a much simpler matter, whereas difficulties associated with high temperatures might make this difficult in the lipid-water system.

Indeed, it has been in the study of nanostructured nonlamellar liquid crystalline structures that the commonality between what had previously been considered intrinsically different—'lipids' and 'surfactants'—came to the forefront, and the two schools of study (lipids, coming from the biological side, and surfactants, coming from the more industrial side) came together as the same nanostructures were observed in lipids as for all surfactants. In addition, it also came to the forefront that certain synthetic surfactants, such as dihexadecyldimethylammonium bromide, which were entirely of synthetic, non-biological origin, showed 'lipid-like' behavior in that hydrophobic solvents were needed for convenient demonstration of their surfactancy. On the other end, certain lipids such as lysolipids, which are clearly of biological origin, display phase behavior more or less typical of water-soluble surfactants. Eventually, it became clear that for the purposes of discussing and comparing self-association and interfacial tension-reducing properties, a more meaningful distinction was between single-tailed and double-tailed compounds, where single-tailed generally implies water-soluble and double-tailed generally oil-soluble.

Thus, in the present context, any amphiphile which at very low concentrations lowers interfacial tensions between water and hydrophobe, whether the hydrophobe be air or oil, and which exhibits reversible self-association into nanostructured micellar, inverted micellar, or bicontinuous morphologies in water or oil or both, is a surfactant. The class of lipids simply includes a subclass consisting of surfactants which are of biological origin.

A number of criteria have been tabulated and discussed in detail by Robert Laughlin for determining whether a given polar group is functional as a surfactant head group, where the definition of surfactant includes the formation, in water, of nanostructured phases even at rather low concentrations. R. Laughlin, Advances in Liquid Crystals, 3:41, 1978. The following listing given by Laughlin gives some polar groups which are not operative as surfactant head groups—and thus, for example, an alkane chain linked to one of these polar groups would not be expected to form nanostructured nonlamellar liquid or liquid crystalline phases—are: aldehyde, ketone, carboxylic ester, carboxylic acid, isocyanate, amide, acyl cyanoguanidine, acyl guanylurea, acyl biuret, N,N-dimethylamide, nitrosoalkane, nitroalkane, nitrate ester, nitrite ester, nitrone, nitrosamine, pyridine N-oxide, nitrile, isonitrile, amine borane, amine haloborane, sulfone, phosphine sulfide, arsine sulfide, sulfonamide, sulfonamide methylimine, alcohol (monofunctional), ester (monofunctional), secondary amine, tertiary amine, mercaptan, thioether, primary phosphine, secondary phosphine, and tertiary phosphine.

Some polar groups which are operative as surfactant head groups, and thus, for example, an alkane chain linked to one of these polar groups would be expected to form nanostructured nonlamellar liquid crystalline phases, are:
  a. Anionics: carboxylate (soap), sulfate, sulfamate, sulfonate, thiosulfate, sulfinate, phosphate, phosphonate, phosphinate, nitroamide, tris(alkylsulfonyl)methide, xanihate;
  b. Cationics: ammonium, pyridinium, phosphonium, sulfonium, sulfoxonium;
  c. Zwitterionics: ammonio acetate, phosphoniopropane sulfonate, pyridinioethyl sulfate;
  d. Semipolars: amine oxide, phosphoryl, phosphine oxide, arsine oxide, sulfoxide, sulfoximine, sulfone diimine, ammonio amidate.

Laughlin also demonstrates that as a general rule, if the enthalpy of formation of a 1:1 association complex of a given polar group with phenol (a hydrogen bonding donor) is less than 5 kcal, then the polar group will not be operative as a surfactant head group.

In addition to the polar head group, a surfactant requires an apolar group, and again there are guidelines for an effective apolar group. For alkane chains, which are of course the most common, if n is the number of carbons, then n must be at least 6 for surfactant association behavior to occur, although at least 8 or 10 is the usual case. Interestingly octylamine, with n=8 and the amine head group which is just polar enough to be effective as a head group, exhibits a lamellar phase with water at ambient temperature, as well as a nanostructured L2 phase. Warnheim, T., Bergenstahl, B., Henriksson, U., Malmvik, A. -C. and Nilsson, P. (1987) J. of Colloid and Interface Sci. 118:233. Branched hydrocarbons yield basically the same requirement on the low n end; for example, sodium 2-ethylhexylsulfate exhibits a full range of liquid crystalline phases. Winsor, P. A. (1968) Chem. Rev. 68:1. However, the two cases of linear and branched hydrocarbons are vastly different on the high n side. With linear, saturated alkane chains, the tendency to crystallize is such that for n greater than about 18, the Krafft temperature becomes high and the temperature range of nanostructured nonlamellar liquid crystalline phases increases to high temperatures, near or exceeding 100° C.; in the context of the present invention, for most applications this renders these surfactants considerably less useful than those with n between 8 and 18. With the introduction of unsaturation or branching in the chains, the range of n can increase dramatically. The case of unsaturation can be illustrated with the case of lipids derived from fish oils, where chains with 22 carbons can have extremely low melting points, due to the presence of as many as 6 double bonds, as in docosahexadienoic acid and its derivatives, which include monoglycerides, soaps, etc. Furthermore, polybutadiene of very high MW is an elastomeric polymer at ambient temperature, and block copolymers with polybutadiene blocks are well known to yield nanostructured nonlamellar liquid crystals. Similarly, with the introduction of branching, one can produce hydrocarbon polymers such as polypropyleneoxide (PPO), which serves as the hydrophobic block in a number of amphiphilic block copolymer surfactants of great importance, such as the Pluronic series of surfactants. Substitution of fluorine for hydrogen, in particular the use of perfluorinated chains, in surfactants generally lowers the requirement on the minimal value of n, as exemplified by lithium perfluourooctanoate (n=8), which displays a full range of liquid crystalline phases, including an intermediate phase which is fairly rare in surfactant systems. As discussed elsewhere, other hydrophobic groups, such as the fused-ring structure in the cholate soaps (bile salts), also serve as effective apolar groups, although such cases must generally be treated on a case by case basis, in terms of determining whether a particular hydrophobic group will yield surfactant behavior.

For single-component block copolymers, relatively simple mean-field statistical theories are sufficient to predict when nanostructure liquid phase and liquid crystalline phase materials will occur, and these are quite general over a wide range of block copolymers. If $\chi$ is the Flory-Huggins interaction parameter between polymer blocks A and B, and N is the total index of polymerization (defined as the number of statistical units, or monomer units, in the polymer chain, consistently with the definition of the interaction parameter) of the block copolymer, then nanostructured nonlamellar liquid crystalline phases are expected when the product $\chi N$ is greater than 10.5. Leibler, L. (1980) Macromolecules 13:1602. For values comparable to, but larger than, this critical value of 10.5, ordered nanostructured (liquid crystalline) phases can occur, including even bicontinuous cubic phases. Hajduk, D. A., Harper, P. E., Gruner, S. M., Honeker, C. C., Kim, G., Thomas, E. L. and Fetters, L. J. (1994) Macromolecules 27:4063.

Polar-apolar interface: In a surfactant molecule, one can find a dividing point (or in some cases, 2 points, if there are polar groups at each end, or even more than two, as in Lipid A, which has seven acyl chains and thus seven dividing points per molecule) in the molecule that divide the polar part of the molecule from the apolar part. In any nanostructured nonlamellar liquid crystalline phase, the surfactant forms monolayer or bilayer films; in such a film, the locus of the dividing points of the molecules describes a surface that divides polar domains from apolar domains; this is called the "polar-apolar interface," or "polar-apolar dividing surface." For example, in the case of a spherical micelle, this surface would be approximated by a sphere lying inside the outer surface of the micelle, with the polar groups of the surfactant molecules outside the surface and apolar chains inside it. Care should be taken not to confuse this microscopic interface with macroscopic interfaces, separating two bulk phases, that are seen by the naked eye.

Bicontinuous: In a bicontinuous structure, the geometry is described by two distinct, multiply-connected, intertwined subspaces each of which is continuous in all three dimensions; thus, it is possible to traverse the entire span of this space in any direction even if the path is restricted to one or other of the two subspaces. In a bicontinuous structure, each of the subspaces is rich in one type of material or moiety, and the two subspaces are occupied by two such materials or moieties each of which extends throughout the space in all three dimensions. Sponge, sandstone, apple, and many sinters are examples of relatively permanent though chaotic bicontinuous structures in the material realm. In these particular examples, one of the subspaces is occupied by a solid that is more or less deformable and the other subspace, though it may be referred to as void, is occupied by a fluid. Certain lyotropic liquid crystalline states are also examples, one subspace being occupied by amphiphile molecules oriented and aggregated into sheet-like arrays that are ordered geometrically, the other subspace being occupied by solvent molecules. Related liquid crystalline states that contain two incompatible kinds of solvent molecules, e.g., hydrocarbon and water, present a further possibility in which one subspace is rich in the first solvent, the other in the second, and the surface between lies within a multiply connected stratum rich in oriented surfactant molecules. Certain equilibrium microemulsion phases that contain comparable amounts of hydrocarbon and water as well as amphiphilic surfactant may be chaotic bicontinuous structures, maintained in a permanent state of fluctuating disorder by thermal motions, for they give no evidence of geometric order but there is compelling evidence for multiple continuity. Bicontinuous morphologies occur also in certain phase-segregated block copolymers. See Anderson, D. M., Davis, H. T., Nitsche, J. C. C. and Scriven, L. E. (1990) Advances in Chemical Physics, 77:337.

Hydrophobe-rich Droplet:

For the case of a hydrophobe-rich droplet, this will be a domain, of size between about 50 nm and 1 centimeter, that will contain as a major component a hydrophobe, thus a component of low solubility in water (less than about 3%), and/or of high octanol-water partition coefficient (Kow greater than or equal to about 10, more preferably greater than about 100), in which are solubilized the active and some fraction (perhaps very small) of each of the components of the second volume. Thus, while thermodynamics dictates that this first volume must contain at least a trace of lipid and the second volume at least a trace of the hydrophobic liquid, the defining feature of the first volume chemistry is that the ratio of hydrophobic liquid to lipid is significantly higher than in the second volume. The solubility of a given active in a mixture of hydrophobe and lipid is typically a very strongly increasing function of an increasing hydrophobe:lipid ratio, because the hydrophobe can generally be chosen specifically for its ability to solubilize the particular active whereas the choice of lipid has much more to do with its ability to form liquid crystals (in the presence of the hydrophobe, in particular). For example, whereas the solubility of the drug paclitaxel in eugenol is over 15% by weight, its solubility in a mixture of 42% egg phosphatidylcholine, 35% eugenol, and 23% water is less than 1.5%; thus the addition of phospholipid and water to the paclitaxel-ineugenol solution induces precipitation of the paclitaxel. The presence of the first volume can thus dramatically increase the overall solubility of the active in the particle, and can yield a substantial and pharmaceutically appropriate concentration of active in cases where the solubility of active in a lipid-rich liquid crystalline phase (in the absence of the first volume) would be prohibitively low, that is, in cases where an therapeutic amount of drug could not be solubilized in a pharmaceutically acceptable amount of liquid crystal.

These requirements can be phrased in terms of phase behavior as follows. There must exist a liquid crystalline phase in equilibrium with a liquid phase which is rich in a hydrophobic liquid that solubilizes the active. Furthermore, if it is desirable to form the particles by a Type I Process as described herein, then there should exist a three-phase equilibrium with these two phases in equilibrium with a polar solvent-rich phase, which is usually a water-rich phase, often over 90% water. On the other hand, if it is desirable to form the particles by a Type II Process, this condition is in some cases superfluous.

The requirement, in this definition, that the hydrophobe-rich liquid droplet have a size (effective diameter) greater than about 50 nm excludes the case where this droplet is a domain of a nanostructure liquid crystalline material, since such a domain would have dimensions less than 50 nm; more importantly, this is already excluded by the requirement that the droplet be a distinct phase from that of the second volume, in rigorous thermodynamic terms. This liquid phase will be hydrophobe-continuous, which is the generalization of the term of art "oil-continuous" to the case where the hydrophobe can be quite different chemically from what is commonly referred to as an "oil". Thermodynamically, this liquid phase can be a reversed micellar solution, a surfactant solution (whether dilute or otherwise, bearing in mind that every surfactant will have some non-zero solubility even if it is vanishingly small), an oil-rich microemulsion, or an L3 phase (of the type referred to as L3*, in publications where L3 and L3* are distinguished).

Polar Solvent-Rich Droplet:

For the case of a polar solvent-rich droplet, this will be a domain, of size between about 50 nm and 1 centimeter, that will contain as a major component a polar solvent (usually water, but possibly one of the other polar solvents listed below), in which are solubilized the active and some fraction (perhaps very small) of each of the components of the second volume. Thus, while thermodynamics dictates that this first volume must contain at least a trace of lipid and the second volume at least a trace of the polar solvent, the defining feature of the first volume chemistry is that the ratio of polar solvent to lipid (or surfactant) is significantly higher than in the second volume. The solubility of a given active in a mixture of polar solvent and lipid is often a very strongly increasing function of an increasing polar solvent:lipid ratio. Thus the presence of the first volume can thus dramatically increase the overall solubility of the active in the particle, and can yield a substantial and pharmaceutically appropriate concentration of active in cases where the solubility of active in a water-rich liquid crystalline phase (in the absence of the first volume) would be prohibitively low, that is, in cases where an therapeutic amount of drug could not be solubilized in a pharmaceutically acceptable amount of liquid crystal.

The requirement, in this definition, that the polar solvent-rich liquid droplet have a size (effective diameter) greater than about 50 $\mu$m excludes the case where this droplet is a domain of a nanostructure liquid crystalline material, since such a domain would have dimensions less than 50 $\mu$m; more importantly, this is already excluded by the requirement that the droplet be a distinct phase from that of the second volume, in rigorous thermodynamic terms. This liquid phase will be polar solvent-continuous, which is the generalization of the term of art "water-continuous" to the case where the polar solvent can be different from water. Thermodynamically, this liquid phase can be a micellar solution, a surfactant solution (whether dilute or otherwise, bearing in mind that every surfactant will have some non-zero solubility even if it is vanishingly small), a water-rich microemulsion, or an L3 phase (of the type referred to as L3, in publications where L3 and L3* are distinguished).

Pharmaceutical active: a compound or agent that exhibits biological activity, including nutritional, nutriceutical and/or pharmacological activity.

Excipients: compound and mixtures of compounds that are used in pharmaceutical formulations that are not the active drugs themselves.

Pharmaceutically-acceptable: a composition in which each excipient is approved by the Food and Drug Administration for use in a pharmaceutical formulation intended for internal use; this also includes compounds that are major components of approved excipients, which are known to be of low toxicity taken internally. A listing of approved excipients, each with the various routes of administration for which they are approved, was published by the Division of Drug Information Resources of the FDA in January, 1996 and entitled "Inactive Ingredient Guide". The existence of a Drug Master File at the FDA is additional evidence that a given excipient is acceptable for pharmaceutical use. In the present context, this listing includes, as approved for internal use (oral, injectable, intraperitoneal, etc.), such excipients as: benzyl benzoate, peppermint oil, orange oil, spearmint oil, ginger fluid extract (also known as essential oil of ginger), thymol, vanillin, anethole, cinnamon oil, cinnamaldehyde, clove oil, coriander oil, benzaldehyde, poloxamer 331 (Pluronic 101), polyoxyl 40 hydrogenated castor oil—indeed, a wide range of surfactants with polyethyleneglycol head groups—calcium chloride and docusate sodium. Absent from the list are a number of apolar or very weakly polar liquids that are more associated with applications as fuels or organic solvents: liquid hydrophobes including toluene, benzene, xylene, octane, decane, dodecane, and the like. In contrast, the hydrophobes and polar hydrophobes that are approved as excipients tend to be natural extracts which have a history of use in foods, nutriceuticals, or pharmaceutics—or early precursors to these disciplines. Examples of compounds that are major components of approved excipients and known to be of low toxicity include: linalool, which is a major component of coriander oil and is the subject of extensive toxicity studies demonstrating its low toxicity; vanillin, which is a major component of the approved excipient 'flavor vanilla' and is one of the major taste components of vanilla-flavored foods and pharmaceutical formulations; and d-limonene, which is a major component of the approved excipient 'essence lemon' approved for use in oral formulations and has extensive everyday applications in which its low toxicity is important. By "component" we mean a molecule that is present as a distinct and individual molecule in a mixture, not as a chemical group in a larger molecule; for example, methanol (methyl alcohol) would not be considered to be a component of methyl stearate. For the purposes of this invention, a compound will be considered to be a pharmaceutically-acceptable excipient if it can be created by a simple ion-exchange between two compounds that are on the FDA listing; thus, for example, calcium docusate is to be considered a pharmaceutically-acceptable excipient since it is a natural result of combining sodium docusate and calcium chloride (in the presence of water, for example).

Coating: In the present context of particles, a "coating" is composed of a material which behaves as a solid in the common sense, and in the engineering viewpoint, of the term "solid", namely that it exhibits a rigidity and permanence that contrasts sharply with low-viscosity liquids, and thus represents a significant diffusional barrier to the passage of compounds across that material, in a way that is intuitively different from any protection that a low-viscosity liquid layer could provide. This common sense understanding of the terms "liquid" and "solid" differs fundamentally from the strict scientific definitions, which refer only to the existence or non-existence of long-range atomic order. Thus, while an amorphous material such as PMMA (Plexiglass) or ordinary glass-particles of which make up an everyday coating known as ceramic glaze-may technically be a liquid, for the purposes of simplifying nomenclature in the context of this invention these materials will be referred to as solids, as they would in ordinary life outside of the physics laboratory. On the other hand, liquid crystals are not to be considered solids (neither in the context of this invention nor in the strict sense of the term), so that the second volume in the instant invention should not, and will not in this text, be referred to as a "coating". The choice of this terminology is driven by the fact that it is desired to reserve the term "coating" for solid materials that are apply outside the second volume. Since this is a particularly important configuration for applying particles of this invention, less confusion will result if the use of the term "coating" is restricted thusly.

Surfactants and Lipids of Utility.

Suitable surfactants or block copolymer components (or mixtures thereof) may include:
a. cationic surfactant
b. anionic surfactant
c. semipolar surfactant
d. zwitterionic surfactant
  i. in particular, a phospholipid
  ii. a lipid mixture containing phospholipids, designed to match the physico-chemical characteristics of a biomembrane
e. monoglyceride
f. PEGylated surfactant
g. one of the above but with aromatic ring
h. block copolymer
  i. with both blocks hydrophobic, but mutually immiscible
  ii. with both blocks hydrophilic, but mutually immiscible,
  iii. with one block hydrophilic and the other hydrophobic, i.e., amphiphilic)
    i. a mixture of two or more of the above.

Suitable lipids include phospholipids (such as phosphatidylcholine, phosphatidylserine, phosphatidylethanolamine, or sphingomyelin), or glycolipids (such as MGDG, diacylglucopyranosyl glycerols, and Lipid A). Other suitable lipids are phospholipids (including phosphatidylcholines, phosphatidylinositols, phosphatidylglycerols, phosphatidic acids, phosphatidylserines, phosphatidylethanolamines, etc.), sphingolipids (including sphingomyelins), glycolipids (such as galactolipids such as MGDG and DGDG, diacylglucopyranosyl glycerols, and Lipid A), salts of cholic acids and related acids such as deoxycholic acid, glycocholic acid, taurocholic acid, etc., gentiobiosyls, isoprenoids, ceramides, plasmologens, cerebrosides (including sulphatides), gangliosides, cyclopentatriol lipids, dimethylaminopropane lipids, and lysolecithins and other lysolipids which are derived from the above by removal of one acyl chain.

Other suitable types of surfactants include anionic, cationic, zwittenionic, semipolar, PEGylated, amine oxide and aminolipids. Preferred surfactants are:
  anionic—sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps of the form $IC_n$, where the chain length n is between 8 and 20 and I is a monovalent counterion such as lithium, sodium, potassium, rubidium, etc.,
  cationic—dimethylammonium and trimethylammonium surfactants of chain length from 8 to 20 and with chloride, bromide or sulfate counterion, myristyl-gammapicolinium chloride and relatives with alkyl chain lengths from 8 to 18, benzalkonium benzoate, double-tailed quaternary ammonium surfactants with chain lengths between 8 and 18 carbons and bromide, chloride or sulfate counterions,
  nonionic PEGylated surfactants of the form $C_nE_m$ where the alkane chain length n is from 6 to 20 carbons and the average number of ethylene oxide groups m is from 2 to 80, ethoxylated cholesterol;
  zwitterionics and semipolars—N,N,N-trimethylaminodecanoimide, amine oxide surfactants with alkyl chain length from 8 to 18 carbons; dodecyldimethylammoniopropane-1-sulfate, dodecyldimethylammoniobutyrate, dodecyltrimethylene di(ammonium chloride); decylmethylsulfonediimine; dimethyleicosylammoniohexanoate and relatives of these zwitterionics and semipolars with alkyl chain lengths from 8 to 20.

Preferred surfactants which are FDA-approved as injectables include benzalkonium chloride, sodium deoxycholate, myristyl-gamma-picolinium chloride, Poloxamer 188, polyoxyl castor oil and related PEGylated castor oil derivatives such as Cremophor EL, Arlatone G, sorbitan monopalmitate, Pluronic 123, and sodium 2-ethylhexanoic acid. Other low-toxicity surfactants and lipids, which are of at least relatively low solubility in water, that are preferred for the present invention for products intended for a number of routes of administration, include: acetylated monoglycerides, aluminum monostearate, ascorbyl palmitate free acid and divalent salts, calcium stearoyl lactylate, ceteth-2, choleth, deoxycholic acid and divalent salts, dimethyldioctadecylammonium bentonite, docusate calcium, glyceryl stearate, stearamidoethyl diethylamine, ammoniated glycyrrhizin, lanolin nonionic derivatives, lauric myristic diethanolamide, magnesium stearate, methyl gluceth-120 dioleate, monoglyceride citrate, octoxynol-1, oleth-2, oleth-5, peg vegetable oil, peglicol-5-oleate, pegoxol 7 stearate, poloxamer 331, polyglyceryl-10 tetralinoleate, polyoxyethylene fatty acid esters, polyoxyl castor oil, polyoxyl distearate, polyoxyl glyceryl stearate, polyoxyl lanolin, polyoxyl-8 stearate, polyoxyl 150 distearate, polyoxyl 2 stearate, polyoxyl 35 castor oil, polyoxyl 8 stearate, polyoxyl60 castor oil, polyoxyl 75 lanolin, polysorbate 85, sodium stearoyl lactylate, sorbitan sesquioleate, sorbitan trioleate, stear-o-wet c, stear-o-wet m, stearalkonium chloride, stearamidoethyl diethylamine (vaginal), steareth-2, steareth-10, stearic acid, stearyl citrate, sodium stearyl fumarate or divalent salt, trideceth 10, trilaneth-4 phosphate, Detaine PB, JBR-99 rhamnolipid (from Jeneil Biosurfactant), glycocholic acid and its salts, taurochenodeoxycholic acid (particularly combined with vitamin E), tocopheryl dimethylaminoacetate hydrochloride, tocopheryl phosphonate, tocopheryl peg 1000 succinate, cytofectin gs, 1,2-dioleoyl-sn-glycero-3-trimethylammonium-propane, cholesterol linked to lysinamide or omithinamide, dimethyldioctadecyl ammonium bromide, 1,2-dioleoyl-sn-3-ethylphosphocholine and other double-chained lipids with a cationic charge carried by a phosphorus or arsenic atom, trimethyl aminoethane carbamoyl cholesterol iodide, lipoic acid, O,O'-ditetradecanoyl-N-(alpha-trimethylammonioacetyl) diethanolamine chloride (DC-6-14), N-[(1-(2,3-dioleyloxy)propyl)]-N-N-N-trimethyl ammonium chloride, N-methyl-4-(dioleyl)methylpyridinium chloride (saint-2), lipidic glycosides with amino alkyl pendent groups, 1,2-dimyristyl-oxypropyl-3-dimethylhydroxyethyl ammonium bromide, bis [2-(11-phenoxyundecanoate)ethyl]-dimethyl ammonium bromide, N-hexadecyl-N-10-[O-(4-acetoxy)-phenyl-undecanoate]ethyl-dimethyl ammonium bromide, bis[2-(11- butyloxyundecanoate)ethyl]dimethylammonium bromide, 3-beta-[N-(N',N'-dimethylaminoethane)-carbamoyl] cholesterol, vaxfectin, cardiolipin, dodecyl-N,N-dimethylglycine, and lung surfactant (Exosurf, Survanta).

Suitable block copolymers are those composed of two or more mutually immiscible blocks from the following classes of polymers: polydienes, polyallenes, polyacrylics and polymethacrylics (including polyacrylic acids, polymethacrylic acids, polyacrylates, polymethacrylates, polydisubstituted esters, polyacrylamides, polymethacrylamides, etc.), polyvinyl ethers, polyvinyl alcohols, polyacetals, polyvinyl ketones, polyvinylhalides, polyvinyl nitriles, polyvinyl esters, polystyrenes, polyphenylenes, polyoxides, polycarbonates, polyesters, polyanhydrides, polyurethanes, polysulfonates, polysiloxane, polysulfides, polysulfones, polyamides, polyhydrazides, polyureas, polycarbodiimides, polyphosphazenes, polysilanes, polysilazanes, polybenzoxazoles, polyoxadiazoles, polyoxadiazoiidines, polythiazoles, polybenzothiazoles, polypyromellitimides, polyquinoxalines, polybenzimidazoles, polypiperazines, cellulose derivatives, alginic acid and its salts, chitin, chitosan, glycogen, heparin, pectin, polyphosphorus nitrile chloride, polytri-n-butyl tin fluoride, polyphosphoryldimethylamide, poly.-2,5-selenienylene, poly-4-n-butylpyridinium bromide, poly-2-N-methylpyridinium iodide, polyallylammonium chloride, and polysodium-sulfonate-trimethylene oxyethylene. Preferred polymer blocks are polyethylene oxide, polypropylene oxide, polybutadiene, polyisoprene, polychlorobutadiene, polyacetylene, polyacrylic acid and its salts, polymethacrylic acid and its salts, polyitaconic acid and its salts, polymethylacrylate, polvethylacrylate, polybutylacrylate, polymethylmethacrylate, polypropylmethacrylate, poly-N-vinyl carbazole, polyacrylamide, polyisopropylacrylamide, polymethacrylamide, polyacrylonitrile, polyvinyl acetate, polyvinyl caprylate, polystyrene, poly-alpha-methylstyrene, polystyrene sulfonic acid and its salts, polybromostyrene, polybutyleneoxide, polyacrolein, polydimethylsiloxane, polyvinyl pyridine, polyvinyl pyrrolidone, polyoxy-tetramethylene, polydimethylfulvene, polymethylphenylsiloxane, polycyclopentadienylene vinylene, polyalkylthiophene, polyalkyl-p-phenylene, polyethylene-altpropylene, polynorbornene, poly-5-((trimethylsiloxy)methyl)norbornene, polythiophenylene, heparin, pectin, chitin, chitosan, and alginic acid and its salts. Especially preferred block copolymers are polystyrene-b-butadiene, polystyrene-b-isoprene, polystyrene-b-styrenesulfonic acid, polyethyleneoxide-b-propyleneoxide, polystyrene-b-dimethylsiloxane, polyethyleneoxide-b-styrene, polynorborene-b-5-((trimethylsiloxy)methyl)norbornene, polyacetylene-b-5 ((trimethylsiloxv)methyl)norbornene, polyacetylene-b-norbornene, polyethyleneoxide-b-norbornene, polybutyleneoxide-b-ethyleneoxide, polyethyleneoxide-b-siloxane, and the triblock copolymer polyisoprene-b-styrene-b-2-vinylpyridine.

Hydrophobes and Oils of Utility in the Present Invention.

It follows from the definitions given above that a hydrophobe must in fact be a hydrophobic compound (partition coefficient Kow>10, preferably >100) which is not a surfactant, i.e., in which any polar group on the molecule is on a par with the following groups listed by Laughlin as being not operative as a surfactant head group: aldehyde, ketone, carboxylic ester, carboxylic acid (in the free acid form), isocyanate, amide, acyl cyanoguanidine, acyl guanylurea, acyl biuret, N,N-dimethylamide, nitrosoalkane, nitroalkane, nitrate ester, nitrite ester, nitrone, nitrosamine, pyridine N-oxide, nitrile, isonitrile, amine borane, amine haloborane, sulfone, phosphine sulfide, arsine sulfide, sulfonamide, sulfonamide methylimine, alcohol (monofunctional), ester (monofunctional), secondary amine, tertiary amine, mercaptan, thioether, primary phosphine, secondary phosphine, and tertiary phosphine. (It should be pointed out that although a single such group on the end of a hydrophobic group, particularly an alkane chain, would not satisfy the definition of a surfactant, the presence of three or more such groups could in fact make an operative surfactant, as in the case of a monoglyceride, for example.) Of these groups, preferred groups for the polar group(s) are, given in approximate order from most preferred to less preferred: alcohol (monofunctional, including phenolic), carboxylic acid, aldehyde, amide, secondary amine, and tertiary amine. The distinction as a preferred group is based mainly on issues of low toxicity, low reactivity, sufficient polarity, and on the lack of tendency to yield high-melting point compounds. In this specification the term "oil" is meant to be equivalent to the term "hydrophobe" except that it is a liquid at, or near, room temperature.

For the pharmaceutically-acceptable hydrophobe of the current invention, there are a number of low-toxicity hydrophobic liquids with polar groups, many of which have a history of safe use in pharmaceutical and/or food products, that could be used. These include essential oils of plant origin, as well as a number of other liquids that are listed on FDA's list entitled Inactive Ingredients for Currently Marketed Drug Products and/or the appropriate sections of the Food Additives Status List. Among these are:

benzyl benzoate, cassia oil, castor oil, cyclomethicone, polypropylene glycol (of low MW), polysiloxane (of low MW), cognac oil (ethyl oenanthate), lemon balm, balsam of Peru, cardamom oleoresin, estragole, geraniol, geraniol acetate, menthyl acetate, eugenol, isoeugenol, petigrain oil, pine oil, rue oil, trifuran, annato extract, turmeric oleoresin, and paprika oleoresin.

Essential oils from plant sources (including their extracts and components, and mixtures thereof) comprise a rather large and chemically diverse group of liquids that include many low-toxicity hydrophobes with polar groups. The term "essential oils" is intended to include essential oils from the following sources:

allspice berry, amber essence, anise seed, arnica, balsam of Peru, basil, bay, bay leaf, bergamot, bois de rose (rosewood), cajeput, calendula (marigold pot), white camphor, caraway seed, cardamon, carrot seed, cedarwood, celery, german or hungarian chamomile, roman or english chamomile, cinnamon, citronella, clary sage, clovebud, coriander, cumin, cypress, eucalyptus, fennel, siberian fir needle, frankincense (olibanum oil), garlic, rose geranium, ginger, grapefruit, hyssop, jasmine, jojoba, juniper berry, lavender, lemon, lemongrass, lime, marjoram, mugwort, mullein flower, myrrh gum, bigarade neroli, nutmeg, bitter orange, sweet orange, oregano palmarosa, patchouly, pennyroyal, black pepper, peppermint, petitegrain, pine needle, poke root, rose absolute, rosehip seed, rosemary, sage, dalmation sage, santalwood oil, sassafras (saffrolefree), spearmint, spikenard, spruce (hemlock), tangerine, tea tree, thuja (cedar leaf), thyme, vanilla extract, vetivert, wintergreen, witch hazel (hamamelia) extract, or ylang ylang (cananga).

The following are components of essential oils: 2,6-dimethyl-2,4,6-octatriene; 4-propenylanisole; benzyl-3-phenylpropenoic acid; 1,7,7-trimethylbicyclo [2.2.1]heptan-2-ol; 2,2-dimethyl-3-methylenebicyclo [2.2.1]heptane; 1,7,7-trimethylbicyclo[2.2.1]heptane; trans-8- methyl-n-vanillyl-6-nonenamide; 2,2,5-trimethylbicyclo [4.1.0]hept-5-ene; 5-isopropyl-2-methylphenol; p-mentha-6,8-dien-2-ol; p-mentha-6,8-dien-2-one; beta-caryophyllene; 3-phenylpropenaldehyde; 3,7-dimethyl-6-octenal; 3,7-dimethyl-6-octen-1-ol; 4-allylanisole; ethyl 3-phenylpropenoic acid; 3-ethoxy-4-hydroxybenzaldehyde; 1,8-cineole; 4-allyl-2-methoxyphenol; 3,7,11-trimethyl-2,6,10 -dodecatrien-1-ol; 1,3,3-trimethylbicyclo [2.2.1]heptan-2-ol; 1,3,3-trimethylbicyclo [2.2.1]heptan-2-one; trans-3,7-dimethyl-2,6-octadien-1-ol; trans-3,7-dimethyl-2,6-octadien-1-yl acetate; 3-methyl-2-(2-pentenyl)-2-cyclopenten-1-one; p-mentha-1,8-diene; 3,7-dimethyl-1,6-octadien-3-ol; 3,7-dimethyl-1,6-octadien-3-yl acetate; p-menthan-3-ol; p-menthan-3-one; methyl 2-aminobenzoate; methyl-3-oxo-2-(2-pentenyl)-cyclopentane acetate; methyl 2-hydroxybenzoate; 7-methyl-3-methylene-1,6-octadiene; cis-3,7-dimethyl-2,6-octadien-1-ol; 2,6,6-trimethylbicyclo [3.1.1]hept-2-ene; 6,6-dimethyl-2-methylenebicyclo[3.1.1]heptane; p-menth-4 (8)-en-3-one; p-menth-1-en-4-ol; p-mentha-1,3-diene; p-menth-1-en-8-ol; and 2-isopropyl-5-methylphenol.

Especially preferred non-surfactant hydrophobes, due to a favorable combination of good drug-solubilizing properties, low toxicity, low water solubility, useful temperature range as a liquid, history of use, and compatibilty with (or induction of) cubic phases, are: benzyl benzoate, estragole, eugenol, isoeugenol, linalool, and the following essential oils: balsam of Peru, basil, bay, bois de rose (rosewood), carrot seed, clovebud, eucalyptus, ginger, grapefruit, hyssop, lemon, mugwort, myrrh gum, bitter orange, oregano, palmarosa, patchouly, peppermint, petitgrain, rosemary, santalwood oil, spearmint, thuja (cedar leaf), thyme, vanilla, and ylang ylang (cananga).

Essential oils from plant sources comprise a rather large and chemically diverse group of liquids that include many low-toxicity oils and components. A good many of these oils are GRAS, Generally Regarded As Safe, by the FDA. When essential oils are mixed with lipid (or surfactant) and polar solvent, at ratios between about 1:2 and 1.5:1, most preferably between 0.7:1 and 1.2:1, the lipid-rich phase is generally either liquid, or liquid crystalline. The inventor has determined that a number of GRAS essential oils tend to form liquid crystalline phases under these conditions, and these include:

Peppermint; spearmint; sweet basil; thyme; ginger; rosemary; fennel; sage; and clove.

Thus, for example, when phosphatidylcholine is mixed with water and one of these oils at a phosphatidylcholine:oil:water ratio of about 42:34:24, liquid crystals generally result at ambient temperature (depending on the source and purity of the oil).

Those GRAS oils which tend to liquify lipid-water mixtures include:

Marjoram; bois de rose (rosewood).

Oil of bay and of vanilla are borderline between these two.

The ability of a number of these GRAS oils to solubilize difficultly-soluble drugs was demonstrated by the current author, by solubilizing paclitaxel in the oils. Here are some selected results:

| Essential oil | Paclitaxel solubility (w/w, approx) |
|---|---|
| Oil of bay | 16% |
| Thyme | 10% |
| Sweet basil | 7% |

A number of very low-toxicity, well-accepted materials-some of which are approved for use in injectable products an be used, and combined, to comprise the hydrophobe(s) of the first volume of the particles in this invention, including but not limited to:

Anethole, Anise alcohol, Anisaldehyde, Beeswax, Benzoin, Benzyl alcohol, Benzyl benzoate, Canola oil, Caproic acid, Caprylic/capric triglyceride, Capsaicin oleoresin, Carnauba wax, Castor Oil, Cinnamaldehyde, Cottonseed oil, Polydimethylsiloxane, Polypropyleneoxide, Eugenol, Lanolin, Menthol, Mineral oil, Paraffin wax, Petroleum wax, Polyisobutylene, Rapeseed oil, Sesame oil, Vegetable oil, Tocopherol, and Tocopherol acetate.

Polar solvents of utility. The polar solvents employed in the practice of the present invention include but are not limited to:
a. water;
b. glycerol;
c. ethylene glycol or propylene glycol;
d. ethylammonium nitrate;
e. one of the acetamide series: acetamide, N-methyl acetamide, or dimethylacetamide;
f. low-molecular weight polyethylene glycol (PEG);
g. a mixture of two or more of the above.

Preferred polar solvents are water, glycerol, ethylene glycol, N-methylacetamide, dimethylacetamide, and polyethylene glycol, since these are considered of low toxicity. However, with the compositions given herein that rely on PEGylated (ethoxylated) surfactants (such as Arlatone and Pluronics), glycerol is generally not compatible.

Active and Bioactive Compounds of Utility.

Examples of drugs with low solubility in aqueous and/or other polar solvents that may be suitable for dissolving in a hydrophobic first volume of the particles and materials of this invention, include but are not limited to:

Nandrolone decanoate, Fentanyl citrate, Testosterone, Albendazole, Dactinomycin, Doxorubicin, Valrubicin, Amphotericin B, Enalaprilat, Docetaxel, Paclitaxel, Vinblastine, Vincristine, Vinorelbine, Batimastat, Eptifibatide, Tirofiban, Saquinavir, Cromolyn, Doxapram, SN-38 (Irinotecan), Teniposide, Trimetrexate, Clyclosporin A, Milrinone lactate, Buprenorphine, Carboplatin, Cisplatin, Estradiol, Hydroxyprogesterone, L-Thyroxine, Midazolam, Bupivacaine (the free base), Ibuprofen, and Ketoprofen.

These compounds represent the following classes of drug: Anabolic steroid, Analgesic, Androgen, Anthelmintic, Antibiotic, Antibiotic (antineoplastic), Antifungal, Antihypertensive, Antimitotic, Antineoplastic, Antiplatelet, Antiviral, Asthma anti-inflammatory, CNS stimulant, DNA topoisomerase inhibitor, Epipodophyllotoxin, Folate antagonist, Immunosuppressant, Inotropic agent, Local anesthetic, Narcotic agonist/antagonist, Platinum complex, Sex hormone, Thyroid hormone.

Examples of water soluble drugs that may be suitable for dissolving in an aqueous or polar first volume of the particles and materials of this invention, include but are not limited to:

Dacarbazine, Ifosfamide, Streptozocin, Thiotepa, Esmolol, Bleomycin sulfate, Amikacin sulfate, Gentamicin, Netilmicin, Streptomycin, Tobramycin, Epirubicin, Idarubicin, Bacitracin, Colistimethate, Oxybutinin, Antithrombin III Human, Heparin, Lepirudin, Adenosine phosphate, Cladribine, Cytarabine, Fludarabine phosphate, Gemcitabine, Pentostatin, Rituximab, Trastazumab, Abciximab, Droperidol, Aurothioglucose, Capreomycin disulfide, Acyclovir, Cidofovir, Pentafuside, Ganciclovir, Aldesleukin, Denileukin, Edrophonium, Infliximab, Topotecan, Hemin, Daunorubicin, Octreotride, Ganirelix acetate, Histrelin acetate, Somatropin, Epoetin, Filgrastim, Oprelvekin, Leuprolide, Basiliximab, Daclizumab, Glatiramer acetate, Interferons, Muromonab-CD3, Nalbuphine, Urofollitropin, Desmopressin, Mitoxantrone, Etanercept, Neostigmine, Epoprostenol, Methoxamine, Versed, Bupivacaine hydrochloride, Heparin, Insulin, Antisense compounds, Ibuprofen, Ketoprofen, Alendronate, Etidronate, Zoledronate, Ibandronate, Risedronate, and Pamidronate.

These compounds represent the following classes of drug: Alkylating agent, Antiadrenergic, Antibiotic, Antibiotic (aminoglycoside), Antibiotic (antineoplastic), Antibiotic (polypeptide), Anticholinergic, Anticoagulant, Anticonvulsant, Antimetabolite, Antineoplastic, Antiplatelet, Antipsychotic, Anesthetic, Antirheumatic, Antituberculosal, Antiviral, Antiviral (HIV), Biological response modifier, Cholinergic muscle stimulant, DNA topoisomerase inhibitor, Enzyme inhibitor, Epipodophyllotoxin, Gastric antisecretory, Gene therapy agents, Gonadotropin-releasing, Growth hormone, Hematopoietic, Hormone, Immunologic agent, Local anesthetic, Narcotic agonist/antagonist, Ovulation stimulant, Pituitary hormone, Platinum complex, TNF inhibitor (arthritis), Urinary cholinergic, Vasodilator, and Vasopressor.

Proteins and nucleic acids (e.g., antisense compounds) represent a particularly important class of actives, both in pharmaceutical applications and in others, and while most proteins can readily be solubilized in liquid crystals, there are a number of reasons for utilizing materials or particles of the instant invention, in which the first volume is polar solvent-rich, typically rich in an aqueous buffer with in some cases the polar solvent glycerol also added. In particular, it may be desirable in many cases to use a liquid crystal with a poresize small enough to either control the release of the macromolecule, or to shield the macromolecule from proteins (e.g., proteases, nucleases, enzymes, etc.), cell types, or other high-MW materials that might othewise degrade, deactivate, or sequester the macromolecule. One example of controlled release would be a liquid crystal with a poresize that is nominally too small to permit substantial release of the macromolecule, but which swells to a larger poresize in response to a physiological condition, such as pH (i.e., the liquid crystal would contain an ionizable bilayer component), or the presence of a specific protein; many proteins are known to swell the poresizes of certain reversed liquid crystals. Higher payloads may be made possible also by the presence of an aqueous core. In addition to well-known proteins (which currently suffer from delivery issues) such as insulin and erythropoietin, there are a number of proteins that are potential therapeutic actives and which could be incorporated into particles of the instant invention, including: Interferon gamma-1b, Altepase, rh tPA, Darbepoeth alfa, Interferon beta-1a, Coagulation factor IX, Coagulation factor VIIa, rh TNF-alpha, Interferon beta-1b, rH factor VII, rH factor VIII, rH factor IX, Somatropin, Alemtuzumab, Imiglucerase, HBsAg, r TNFR-IgG fragment, rh EPO, Follitropin alpha, Follitropin beta, glucagon, trastuzumab, Insulin lispro, rh insulin, Interferon alfacon-1, rh human insulin, Interferon alfa-2b, Anakinra, Insulin glargine, r GM-CSF, rh insulin lispro, r OspA, r IL-2, Rituximab, Oprelvekin, Filgrastim, fh insulin aspart, Muromomab CD3, Peginterferon, rH BsAg, rh EPO, Aldesleukin, Somatrem, Domase-alpha, Dnase, rh Follicle Stimulating hormone, Retaplase, r tPA, Ribavirin, USP and Interferon alfa-2b recombinant, r HBsAg, Antihemophilic factor, Moroctocog-alfa, Becaplermin, rh PDGF, Infliximab, Abciximab, Reteplase recombinant, Reteplase, r tPA, Hirudin, Rituximab, Interferon alfa-2a, Basiliximab, Palivizumab, Tenecteplase, r HBs Ag, r HBs Ag, Fomivirsen, Daclizumab In view of the demanding requirements for the delivery of pharmaceuticals in the treatment of cancers, the advantages and flexibility of the present invention make it particularly attractive in the delivery and controlled release of antineoplastic agents, such as for example, the following:

Alkylating Agents

Alkyl Sulfonates—Busulfan, Improsuflan, Piposulfan.

Aziriaines—Benzodepa, Carboquone, Meturedepa, Uredepa,

Ethyleneimines and Methylmelamines—Altretamine, Triethylenemelamine, Triethylenephosphoramide, Triethylenethiophosphoramide, Trimethylolmelamine, Nitrogen Mustards—Chlorambucil, Chloramphazine, Cyclophosphamide, Estramustine, Ifosfamide, Mechlorethamine, Mechlorethamine Oxide Hydrochloride, Melphalan, Novembichin, Phenesterine, Prednimustine, Trofosfamide, Uracil, Mustard.

Nitrosourea—Carmustine, Chlorozotocin, Fotemustine, Lomustine, Nimustine, Ranimustine, Others—Dacarbazine, Mannomustine, Mitobronitol, Mitolactol, Pipobroman.

Antibiotics—Actacinomveins—Actinomycin FI, Anthramycin, Azaserine, Bleomvyins, Cactinomycin, Carubicin, Carzinophilin, Chromomycins, Dactinomycin, Daunorubicin, 6-Diazo-5-OXO-Leucine, Doxorubicin, Epirubicin, Mitomycins, Mycophenolic Acid, Nogalamycin, Olivomycins, Peplomycin, Plicarmcin, Porfiromycin, Puromycin, Streptonigrin, Streptozocin, Tubercidin, Ubenimex, Zinostatin, Zorubicin.

Antimetabolites

Folic Acid Analogs—Denopterin, Methotrexate, Pteropterin, Trimetrexate.

PurineAnalogs—Fludarabine, 6-Mercaptopurine, Thiamiprine, Thioguanine,

Pyrimidine Analogs—Ancitabine, Azacitidine, 6-Azauridine, Carrnofur, Cytarabine, Doxifluridine, Enocitabine, Floxuridine, Fluorouracil, Tegafur.

Enzymes—L-Asparaginase, etc.

Others—Aceglatone, Amsacrine, Bestrabucil, Bisantrene, Carboplatin, Cisplatin, Defosfamide, Demecolcine, Diaziquone, Eflorithine, Elliptinium Acetate, Etoglucid, Etoposide, Gallium Nitrate, Hydroxyurea, Interferon-ot, Interferon-P, Interferon-y, Interleukin-2, Lentinan, Lonidamine, Mitoguazone, Mitoxantrone, Mopidamol, Nitracrine, Pentostatin, Phenamet, Pirarubicin, Podophyllinic Acid, 2-Ethylhydrazide, Procarbazine, PSK09, Razoxane, Sizofiran, Spirogermanium, Taxol, Teniposide, Tenuazonic Acid, Triaziquone, 2,2',2,1,1-Trichlorotriethylamine, Urethan, Vinblastine, Vincristine. Vindesine.

Androgens—Calusterone, Dromostanolone Propionate, Epitiostanol, Mepitiostane. Testolactone.

Antiadrenals—Aminoglutethimide, Mitotane, Trilostane.

Andandrogens—Flutamide, Nilutamide.

Antiestrogens—Tamoxifen, Toremifene.

Estrogens—Fosfestrol, Hexestrol, Polyestradiol Phosphate.

LH-RH Analogs—Buserelin, Goserelin, Leuprolide, Triptorelin.

Progestogens—Chlormadinone Acetate, Medroxyprogesterone, Megestrol Acetate, Melengestrol.

Antineoplastic (Radiation Source) Americium, Cobalt, $^{131}$I-Ethiodized Oil, Gold (Radioactive, Colloidal), Radium, Radon, Sodium Iodide (Radioactive), Sodium Phosphate (Radioactive), Antineoplastic Adjuncts
Folic Acid Replenisher—Folinic Acid,
Uroprotective—Mesna.

It should be pointed out that although this invention contemplates that the bulk of the active compound will usually be present (at any given instant) in the first volume, thermodynamics dictates that some must also be present in the second volume. Indeed, there are embodiments contemplated in this invention in which the first volume will serve primarily as a bioactive compound (e.g., absorption enhancer, P-gp inhibitor, etc.), or will serve a physical function (such as adjusting the density or some optical property), and most of the active drug will be disposed in the second volume.

Certain actives are of sufficiently low solubility even in appropriate liquid crystalline phases, and/or require sufficiently high therapeutics doses in humans (several hundred milligrams), that the use of particles of this invention is especially advantageous. This is a wide range of compounds, but a list of representative compounds would include paclitaxel (and other taxanes), vancomycin, ceftriaxone (and other cephalosporins), dantrolene, camptothecins, and platinum anticancer compounds such as cisplatin.

The Nonlamellar Liquid Crystalline Phases of Utility.

As the second volume, the nanostructured nonlamellar liquid crystalline phase material may be a. a nanostructured normal or reversed cubic phase material, b. a nanostructured normal or reversed hexagonal phase material, or c. a nanostructured normal or reversed intermediate phase material.

The nanostructured nonlamellar liquid crystalline phases are characterized by domain structures, composed of domains of at least a first type and a second type (and in some cases three or even more types of domains) having the following properties:

a) the chemical moieties in the first type domains are incompatible with those in the second type domains (and in general, each pair of different domain types are mutually incompatible) such that they do not mix under the given conditions but rather remain as separate domains; (for example, the first type domains could be composed substantially of polar moieties such as water and lipid head groups, while the second type domains could be composed substantially of apolar moieties such as hydrocarbon chains; or, first type domains could be polystyrene-rich, while second type domains are polyisoprene-rich, and third type domains are polyvinylpyrrolidone-rich);

b) the atomic ordering within each domain is liquid-like rather than solid-like, lacking lattice-ordering of the atoms; (this would be evidenced by an absence of sharp Bragg peak reflections in wide-angle x-ray diffraction);

c) the smallest dimension (e.g., thickness in the case of layers, diameter in the case of cylinders or spheres) of substantially all domains is in the range of nanometers (viz., from about 1 to about 100 nm); and d) the organization of the domains conforms to a lattice, which may be one-, two-, or three-dimensional, and which has a lattice parameter (or unit cell size) in the nanometer range (viz., from about 5 to about 200 nm); the organization of domains thus conforms to one of the 230 space groups tabulated in the International Tables of Crystallography, and would be evidenced in a well-designed small-angle x-ray scattering (SAXS) measurement by the presence of sharp Bragg reflections with d-spacings of the lowest order reflections being in the range of 3–200 nm.

Normal hexagonal phase: The normal hexagonal phase is characterized by:

1. Small-angle x-ray shows peaks indexing as $1:\sqrt{3}:2\sqrt{7}:3\ldots$; in general, $(h^2+hk+k^2)$, where h and k are integers—the Miller indices of the two dimensional symmetry group.

2. To the unaided eye, the phase is generally transparent when fully equilibrated, and thus often considerably clearer than any nearby lamellar phase.

3. In the polarizing optical microscope, the phase is birefringent, and the well-known textures have been well described by Rosevear, and by Winsor (e.g., Chem. Rev. 1968, p.1). The most distinctive of these is the "fan-like" texture. This texture appears to be made up of patches of birefringence, where within a given patch, fine striations fan out giving an appearance reminiscent of an oriental fan. Fan directions in adjacent patches are randomly oriented with respect to each other. A key difference distinguishing between lamellar and hexagonal patterns is that the striations in the hexagonal phase do not, upon close examination at high magnification, prove to be composed of finer striations running perpendicular to the direction of the larger striation, as they do in the lamellar phase.

For normal hexagonal phases in surfactant-water systems:

1. viscosity is moderate, more viscous than the lamellar phase but far less viscous than typical cubic phases (which have viscosities in the millions of centipoise).

2. the self-diffusion coefficient of the surfactant is slow compared to that in the lamellar phase; that of water is comparable to that in bulk water.

3. the $^2$H NMR bandshape using deuterated surfactant shows a splitting, which is one-half the splitting observed for the lamellar phase.

4. in terms of phase behavior, the normal hexagonal phase generally occurs at moderate surfactant concentrations in single-tailed surfactant/water systems, typically on the order of 50% surfactant. Usually the normal hexagonal phase region is adjacent to the micellar (L1) phase region, although non-bicontinuous cubic phases can sometimes occur in between. In double-tailed surfactants, it generally does not occur at all in the binary surfactant-water system For hexagonal phases in single-component block copolymer systems, the terms "normal" and "reversed" do not generally apply (although in the case where one block is polar and the other apolar, these qualifiers could be applied in principle). The shear modulus in such a hexagonal phase is generally higher than a lamellar phase, and lower than a bicontinuous cubic phase, in the same system. In terms of phase behavior, the hexagonal phases generally occurs at volume fractions of the two blocks on the order of 35:65. Typically, two hexagonal phases will straddle the lamellar phase, with, in each case, the minority component being inside the cylinders (this description replacing the 'normal/reversed' nomenclature of surfactant systems).

Reversed hexagonal phase: In surfactant-water systems, the identification of the reversed hexagonal phase differs from the above identification of the normal hexagonal phase in only two respects:

1. The viscosity of the reversed hexagonal phase is generally quite high, higher than a typical normal hexagonal phase, and approaching that of a reversed cubic phase. And, 2. In terms of phase behavior, the reversed hexagonal phase generally occurs at high surfactant concentrations in double-tailed surfactant/water systems, often extending to, or close to, 100% surfactant. Usually the reversed hexagonal phase region is adjacent to the lamellar phase region which occurs at lower surfactant concentration, although bicontinuous reversed cubic phases often occur in between. The reversed hexagonal phase does appear, somewhat surprisingly, in a number of binary systems with single-tailed surfactants, such as those of many monoglycerides (include glycerol monooleate), and a number of nonionic PEG-based surfactants with low HLB.

As stated above in the discussion of normal hexagonal phases, the distinction between 'normal' and 'reversed' hexagonal phases makes sense only in surfactant systems, and generally not in single-component block copolymer hexagonal phases.

Normal bicontinuous cubic phase: The normal bicontinuous cubic phase is characterized by:

1. Small-angle x-ray shows peaks indexing to a three-dimensional space group with a cubic aspect. The most commonly encountered space groups, along with their indexings, are: Ia3d (#230), with indexing $\sqrt{6}:\sqrt{8}:\sqrt{14}:4:\ldots$; Pn3m (#224), with indexing $\sqrt{2}:\sqrt{3}:2:\sqrt{6}:\sqrt{8}:\ldots$; and Im3m (#229), with indexing $\sqrt{2}:\sqrt{4}:\sqrt{6}:\sqrt{8}:\sqrt{10}:\ldots$ 2. To the unaided eye, the phase is generally transparent when fully equilibrated, and thus often considerably clearer than any nearby lamellar phase.

3. In the polarizing optical microscope, the phase is non-birefringent, and therefore there are no optical textures.

For normal bicontinuous cubic phases in surfactant-water systems:

1. viscosity is high, much more viscous than the lamellar phase and even more viscous than typical normal hexagonal phases. Most cubic phase have viscosities in the millions of centipoise.

2. no splitting is observed in the NMR bandshape, only a single peak corresponding to isotropic motion.

3. in terms of phase behavior, the normal bicontinuous cubic phase generally occurs at fairly high surfactant concentrations in single-tailed surfactant/water systems, typically on the order of 70% surfactant with ionic surfactants. Usually the normal bicontinuous cubic phase region is between lamellar and normal hexagonal phase regions, which along with its high viscosity and non-birefringence make its determination fairly simple. In double-tailed surfactants, it generally does not occur at all in the binary surfactant-water system.

For bicontinuous cubic phases in single-component block copolymer systems, the terms "normal" and "reversed" do not generally apply (although in the case where one block is polar and the other apolar, these qualifiers could be applied in principle). The shear modulus in such a bicontinuous cubic phase is generally much higher than a lamellar phase, and significantly than a hexagonal phase, in the same system. In terms of phase behavior, the bicontinuous cubic phases generally occur at volume fractions of the two blocks on the order of 26:74. In some cases, two bicontinuous cubic phases will straddle the lamellar phase, with, in each case, the minority component being inside the cylinders (this description replacing the 'normal/reversed' nomenclature of surfactant systems), and hexagonal phases straddling the cubic-lamellar-cubic progression.

Reversed bicontinuous cubic phase: In surfactant-water systems, the identification of the reversed bicontinuous cubic phase differs from the above identification of the normal bicontinuous cubic phase in only one respect.

In terms of phase behavior, the reversed bicontinuous cubic phase is found between the lamellar phase and the reversed hexagonal phase, whereas the normal is found between the lamellar and normal hexagonal phases; one must therefore make reference to the discussion above for distinguishing normal hexagonal from reversed hexagonal. A good rule is that if the cubic phase lies to higher water concentrations than the lamellar phase, then it is normal, whereas if it lies to higher surfactant concentrations than the lamellar then it is reversed. The reversed cubic phase generally occurs at high surfactant concentrations in double-tailed surfactant/water systems, although this is often complicated by the fact that the reversed cubic phase may only be found in the presence of added hydrophobe ('oil') or amphiphile. The reversed bicontinuous cubic phase does appear in a number of binary systems with single-tailed surfactants, such as those of many monoglycerides (include glycerol monooleate), and a number of nonionic PEG-based surfactants with low HLB.

It should also be noted that in reversed bicontinuous cubic phases, though not in normal, the space group #212 has been observed. This phase is derived from that of space group #230.

As stated above in the discussion of normal bicontinuous cubic phases, the distinction between 'normal' and 'reversed' bicontinuous cubic phases makes sense only in surfactant systems, and generally not in single-component block copolymer bicontinuous cubic phases.

Normal discrete (non-bicontinuous) cubic phase: The normal non-bicontinuous cubic phase is characterized by:

1. Small-angle x-ray shows peaks indexing to a three-dimensional space group with a cubic aspect. The most commonly encountered space group in surfactant systems is Pm3n (#223), with indexing $\sqrt{2}:\sqrt{4}:\sqrt{5}:\ldots$ In single-component block copolymers, the commonly observed space group is Im3m, corresponding to body-centered, sphere-packings, with indexing $\sqrt{2}:\sqrt{4}:\sqrt{6}:\sqrt{8}:\ldots$ 2. To the unaided eye, the phase is generally transparent when fully equilibrated, and thus often considerably clearer than any associated lamellar phase.

3. In the polarizing optical microscope, the phase is non-birefringent, and therefore there are no optical textures.

For normal discrete cubic phases in surfactant-water systems:

1. viscosity is high, much more viscous than the lamellar phase and even more viscous than typical normal hexagonal phases. Most cubic phase have viscosities in the millions of centipoise, whether discrete or bicontinuous.

2. also in common with the bicontinuous cubic phases, there is no splitting in the NMR bandshape, only a single isotropic peak.

3. in terms of phase behavior, the normal discrete cubic phase generally occurs at fairly low surfactant concentrations in single-tailed surfactant/water systems, typically on the order of 40% surfactant with ionic surfactants. Usually the normal discrete cubic phase region is between normal micellar and normal hexagonal phase regions, which along with its high viscosity and non-birefringence make its determination fairly simple. In double-tailed surfactants, it generally does not occur at all in the binary surfactant-water system.

For discrete cubic phases in single-component block copolymer systems, the terms "normal" and "reversed" do not generally apply (although in the case where one block is polar and the other apolar, these qualifiers could be applied in principle). The shear modulus in such a discrete cubic phase is generally dependent almost entirely on the shear modulus of the polymer that forms the blocks in the continuous phase. In terms of phase behavior, the discrete cubic phases generally occur at very low volume fractions of one or other of the two blocks, on the order of 20% or less.

Reversed discrete cubic phase: The reversed discrete cubic phase is characterized by:

In surfactant-water systems, the identification of the reversed discrete cubic phase differs from the above identification of the normal discrete cubic phase in three respects:

1. In terms of phase behavior, the reversed discrete cubic phase if found between the lamellar phase and the reversed hexagonal phase, whereas the normal is found between the lamellar and normal hexagonal phases; one must therefore make reference to the discussion above for distinguishing normal hexagonal from reversed hexagonal. A good rule is that if the cubic phase lies to higher water concentrations than the lamellar phase, then it is normal, whereas if it lies to higher surfactant concentrations than the lamellar then it is reversed. The reversed cubic phase generally occurs at high surfactant concentrations in double-tailed surfactant/water systems, although this is often complicated by the fact that the reversed cubic phase may only be found in the presence of added hydrophobe ('oil') or amphiphile. The reversed discrete cubic phase does appear in a number of binary systems with single-tailed surfactants, such as those of many monoglycerides (include glycerol monooleate), and a number of nonionic PEG-based surfactants with low HLB.

2. The space group observed is usually Fd3m, #227.

3. The self-diffusion of the water is very low, while that of any hydrophobe present is high; that of the surfactant is generally fairly high, comparable to that in the lamellar phase. As stated above in the discussion of normal discrete cubic phases, the distinction between 'normal' and 'reversed' discrete cubic phases makes sense only in surfactant systems, and generally not in single-component block copolymer discrete cubic phases.

Intermediate Phases:

These phases occur quite rarely, and when they are found they generally occupy very narrow regions in the phase diagram. Presently the structures of many of these are unknown or under debate. The intermediate phases can be classified as follows:

Normal int(1) phases occur at lower surfactant concentration than the normal bicontinuous cubic phase, adjacent to the hexagonal phase. Viscosity is generally low or moderately low, no higher than that of the normal hexagonal phase. The phase is birefringent, with textures typically similar to those of the hexagonal phase. Self-diffusion of the components is very similar to those in the hexagonal phase. Small-angle x-ray shows a lower-symmetry space group than the cubic phases, typically monoclinic. Fairly sophisticated NMR bandshape and SAXS analyses can be used to distinguish this phase from the normal hexagonal phase. See Henriksson, U., Blackmore, E. S., Tiddy, G. J. T. and Soderman, O. (1992) J. Phys. Chem. 96:3894. Typically bandshape splittings will be intermediate between those of hexagonal and the zero splitting of the isotropic phase, which provides good evidence of an intermediate phase.

Normal int(2) is found at higher concentrations than the normal bicontinuous cubic phase, adjacent to the lamellar phase. These bear close resemblance, both in terms of property and probably also in terms of structure, to the normal bicontinuous cubic phases, except that they are birefringent, and show differences in NMR bandshape and SAXS analyses. Optical textures are somewhat unusual, in some cases resembling lamellar textures and in some resembling hexagonal, but these can be considerably coarser than either of the more common phases. As in the int(1) phases, the space group is of lower symmetry, typically rhombohedral or tetragonal, requiring two unit cell parameters for characterization, and making SAXS analysis difficult. In general, if the squares of the d-spacing ratios cannot be fit to a simple integral scheme, then an intermediate phase structure is suspect.

Reversed int(2) is found at lower concentrations than the reversed bicontinuous cubic phase, adjacent to the lamellar phase. These are birefringent, and show unusual in NMR bandshape and SAXS analyses. As in the int(1) and int(2) phases, the space group is of lower symmetry, typically rhombohedral or tetragonal, requiring two unit cell parameters for characterization, and making SAXS analysis difficult, SAXS analysis difficult, though the presence of Bragg peaks in the SAXS spectrum which do not index to a cubic or hexagonal lattice (which have only one lattice parameter) is, together with optical birefringence, indication of an intermediate phase. Space groups which are likely for bicontinuous intermediate phases have been discussed in a publication by the present author. D. M. Anderson, Supplement to J. Physique, Proceedings of Workshop on Geometry and Interfaces, Aussois, France, September 1990, C7-1–C7-18.

Incorporation of Targeting Groups and Other Bioactive Compounds.

The presence of a well-defined liquid crystalline phase, particularly in the case of a reversed liquid crystalline phase, makes it possible for embodiments of this invention to incorporate, in a number of different ways, chemicals or chemical groups that can be invoked to target particles temporally and spatially, for example, to target particles to specific sites in the body. Antibodies, steroids, hormones, oligo- or polysaccharides, nucleic acids, vitamins, immunogens, and even nanoprobes are all examples of a wide range of materials that could be incorporated into the liquid crystalline particle component of particles of the instant invention. Similarly, other functional compounds (which are not the active or drug itself) incorporated on or in the second volume 20 could serve important functions, such as: absorption enhancers and efflux protein inhibitors such as oil of ginger could be present so as to increase permeability of absorption barriers (lipid bilayers, gap junctions) prior to or concomitant with the release of drug; proteins or other adsorption-modulating materials could be incorporated that would inhibit unfavorable binding of endogenous proteins such as albumin; adjuvants could be incorporated that would enhance the effect of vaccine components or other immune modulating materials.

Antibodies are broadly useful for targeting to specific sites or molecules in the body or other environments, and can be incorporated at various sites in a particle, including within or at the surface of the liquid crystalline second volume, or associated with a coating if one is applied. In particular, intact antibodies with their more hydrophobic Fc fragment are prone to partitioning into matrices of the type used in this invention, and furthermore it is well known that antibodies can be adsorbed or attached (including covalently) to solid surfaces with retention of binding and binding specificity. For example, antibodies are currently available for each of the following materials, so that these antibodies can be incorporated into the liquid crystalline domains of the instant invention:

8-hydroxy-guanosine, AAV (adeno virus), ACHE (acetylcholinesterase), ACHER (acetylcholine and NMDA receptor), acid phosphatase, ACTH, Actin (cardiac, smooth muscle, and skeletal), Actinin, Adeno-associated virus, adenosine deaminase, Adipophilin (adipocy differentiation related peptide), Adrenomedulin 1-6, Advanced glycation end-products (AGE), alanine transaminase, albumin, alcohol dehydrogenase, aldehyde dehydrogenase, aldolase, Alfentanil AB, Alkaline Phosphatase, alpha Actinin, Alpha-1-anti-chymotrypsin, alpha-1-antitrypsin, alpha-2-macroglobulin, alpha-catenin, beta-catenin and gamma cateinin, Alpha-Fetoprotein, Alpha-fetoprotein receptor, Alpha-Synuclein, Alzheimer Precursor Protein 643–695(Jonas), Alz-90, Precursor Protein A4, amino acid oxidase, Amphetamine, amphiphysin, amylase, amylin, Amylin Peptide, Amyloid A and P, Amyloid precursor protein, ANCA (Proteinase PR3), androgen receptor, Angiogenin, Angiopoietin-1 and Angiopoietin-2 (ang-1/Ang-2), Angiotensin Converting Enzyme, Angiotensin II Receptor At1 and At2, Ankyrin, Apolipoprotein D, Apolipoprotein E, arginase I, B Arrestin 1 and B Arrestin 2, ascorbate oxidase, asparaginase, aspartate transaminase, Atpase (p97), atrial Natriuretic Peptide, AU1 and AU5, Bacillus Antracis (Anthrax) and Bacill, antracis lethal factor, Bad, BAFF, Bag-1, BAX, bcl-2, BCL-Xl, B Nerve Growth Factor, beta Catenin, Benzoylecognine (cocaine), beta-2 microglobulin, beta Amyloid, Galactosidase, beta Glucuronidase, Blood Group antigens (RhoD, A1,A2 A1,A2,A3, B, A, Rh(0)D, RhoC, B M, N), Blood Group H antigen, bombesin and bombesin/gastrin releasing peptide, Bone Morphogenetic Protein (BMP), Bone marrow stromal cell antigen, BST-3, Borrelia burgdorferi garinii, borrelia burgdorferi sensustricto, Bovine Serum, Bradykinin Receptor B2, Brain derived neutrophic factor, Bromodeoxyuridine, CA 19-9, CA 125, CA 242, CA 15-3, CEA, Ca+ ATPase, Calbindin D-28K (Calcium binding protein), Calgranulin A, Cadherin, CD 144, Calcineurin, Calcitonin, Calcitonin gene related peptide, Calcium Channel, Caldesmon, Calmodulin, Calnexin, Calpactin light chain, Calpain, Calpastatin, Calreticulin, Calretinin, Calsequestrin, Cam Kinase II, Canine Distemper virus, carbonic anhydrase I and II, Carboxypeptidase A, B and E, Carboxypeptidase Y, Cardi, Troponin C and T, cardiotrophin-1, Caspase 3 (CPP32), Catalase, Catenins, Caveolin 1, 2 a and 3, CCR, CD44 (HCAM), CD56 (NCAM), CDK2, CDK4 (Cyclin Dependent Kinase C), Carcinoembryonic Antigen, Cellular antigens, CFTR (cystic fibrosis transmembrane conductance protein), chemokine receptors, chlamydia, CHO cell (Chinese Hamster Ovary Cell) Proteins, cholera toxin, choline oxidase, Chondroitin, Chloramphenic, Acetyltransferase (CAT), Chromogranin A, B and C (Secreogranin III), cholesterol oxidase, Chymotrypsin, Cingulin, Citrate Synthethetase, C-kit/stem cell factor receptor, CK-MB, Clathrin Antigen, Clostridium Botulinum D Toxoid, Clusterin, C-MYC, CNS Glycoprotein 130 kD, Collagen Type IV and Type VII, Complement 5b neoepitope, Complement C3a, C3b, C5 and C9, complexin 2, Corticoliberin (CRF), C-peptide, CRF (Corticotropin Releasing Factor), Corticotropin releasing factor receptor, COX-1 and Cox-2, CPP32 (also known as Caspase 3, apopain or Yama), Creatine transporter, C-Reactive Protein (CRP), Cryptosporidium, CXCR-5, Cyclin A, Cyclin D1, D2 and D3, Cyclosporine A, Cylicin I, Cytochrome B5, Cytochrome C, Cytochrome oxidase, Cytochrome P450, Cytokeratin Types I and II, Cytomegalovirus, DAP Kinase, Dendritic cells, Desmin, Desmocollin 1, 2 and 3, Desmoglein 1, 2 and 3, Desmoplakin 1 and 2, Dextranase, DHT (Dihydrotestosterone), Dihydrofolate Reductase (DHFR), Dioxin, Diptheria toxin, Distemper, DJ-1, DNA single-stranded, DNA double stranded, DNA Topoisomerase II and Phospho-topoisomerase IIa+II alpha/beta, Dopamine, Dopamine Beta-Hydroxylase, Dopamine Receptor, Dopamine Transporter, Drebrin, Dysferlin, Dystrobrevin, *E.Coli* expression plasmid, Elastase, Elastin, Endocrine Granu, Constituent (EGC), Endorphin, Endothelial cell, Endothelin, Endothelin Receptor, Enkephalin, enterotoxin *Staphylococcus aureus*, Eosinophil Peroxidase, Eosinophil derived neurotox, (EDN), Eotaxin, Eotaxin-2, Epidermal Growth Factor, Epidermal Growth Factor 2, epidermal growth factor receptor, testostosterone, Epithelial Proliferating antigen, Epithelium Specific Antigen, c-MYC, HA. 1, VSV-G Tag, Glu-Glu, EEEYMPME, Thioredoxine (trx), Epstein Barr virus and Epstein Barr Virus capsid antigen gp120, ERK (ERK1, ERK2, ERK3, pan ERK also called MAP kinase), Erythrocytes, Erythropoietin (EPO), Esterase, Estradiol, Estriol, Estrogen Receptor, Estrone, Ets-1 transcription, F1 antigen *Yersina pestis*, Factor 5, Factor VII, Factor VIII, Factor 9, Factor 10, Factor 11, Factor 12, Factor XIII, FAK (Focal Adhesion Kinase), FAS (CD95), FAS-L (CD178), Fascin, Fatty Acid Binding Protein, Ferritin, Fetal Hemoglobin, Fibrillin-1, Fibrinogen, Fibroblasts, Fibroblast Growth Factor, FGF-9, Fibronectin, Filamin, FKBP51, FKBP65, FK506, FLK1, flt-1 FLt-4 and FLT-3/FLK-2, FLT 3 Ligand, Fluorescein (FITC), FODRIN, Folate, Folate Binding Protein, fractalkine, frequenin, Frizzled, Fructose-6-p-kina, FSH, Fusin (CXCR4), GABA A and GABA B Receptor, Galectin, galanin, gastrin, GAP-43, G-CSF, G-CSF receptor, gelsolin, GIP (gastric inhibitory peptide), GO-protein (bovine), GDNF, GDNF-Receptor, Giardia intestinalis, Glial fibrillary acidic Protein, Glial filament protein, Glucagon/Glycentin, Glucose oxidase, Glucose 6 Phosphate Dehydrogenase, Gluco, Tranporter GLUT 1–4, GLUT 1–5, Glutamate Dehydrogenase, Glutamic Acid decarboxyla (GAD), Glutathione, Glyceraldehyde-3-phosphate dehydrogenase GAPDH, Glycerol-3-phosphate dehydrogenase, Glycerol kinase, glycine transporter (GLYT1, GLYT2), Glycogen Phosphoralase Isoenzyme BB (GPBB), Glycophorin A (CD235a), GM-CSF, C receptor alpha, Golgi Complex, Gonadotropin-Releasing Hormone Receptor (GnRHR), GP130, Granzyme, GRB2, GRB1, Green Fluorescent Protein (GFP), Growth Hormone, Growth Hormone Receptor, Growth Hormone Releasing factor, GRP78, Hantavirus, HCG, HDL (high density lipoprotein), Heat Shock Protein HSP-27, HeK 293 Host Cell Proteins, Helodermin, helospectin, Hemeoxygenase, Hemoglobin, Heparin, Hepatitis A, Hepatitis B Core Antigen, Hepatitis B virus surface antigen, Hepatitis C virus, Hepatistis E virus, Hepatitis G Virus, Hepatocyte Growth Factor, Heregulin (Neu differentiation factor/Neuregulin), Herpes Simplex Virus, Hexokinase, Histamine, His Tag, 6-His vector tags, HIV-1 p24, p55/17, gp41, gp120, tat, nef, rev, HIV reverse transcriptase, HLA Class I, HLA Class II, HLA-DM, HLA DQw1, HLA DRw 52, Peroxidase, HPV 16 Late I Protein, human free kappa light chains, human lambda light chains, Human IgA, human I heavy chain, human IgA1, human IgD, human IgE, human IgG heavy chain, human IgG1, human IgG3, human IgG4, human IgM, human IgM heavy chain, human J chain, human kappa lig, chains, human lambda light chains, Human Serum Amyloid P, Human Serum Amyloid P, Interleukin 1 beta converting enzyme, ICH-1 (caspase 2), Indian Hedgehog Protein (IHH), Influenza virus, Inhibin, Insulin, insulin like growth factor II, insulin growth factor binding protein 1, 2, 3, 4 or 5, insulin like growth factor, insulin like growth factor I receptor, insulin receptor, insulin/proinsulin, Interferon alpha, interferon alpha receptor, Interferon beta, Interferon gamma, interferon gamma receptor alpha and beta, Interleukin 1 alpha, Interleukin Receptor alpha type II, Interleukin 1-beta, Interleukin 10, interleukin 10 receptor, Interleukin 11, Interleukin 12, interleukin 12 receptor, Interleukin 13, Interleukin 15, Interleukin 16, Interleukin 17, Interleukin 18, Interleukin 2, Interleukin 2 receptor alpha, Interleukin receptor alpha chain (CD25), Interleukin 2 receptor beta, Interleukin 2 receptor beta chain(CD122), Interleukin 2 receptor gamma, Interleukin 3, Interleukin 3/interleukin 5/GM-CSF Receptor common chain, Interleukin 4, Interleukin 5, Interleukin 6, Interleukin 6 receptor alpha chain, Interleukin 7, Interleukin 7 receptor alpha, Interleukin 8, Interleukin 8 receptor, Interleukin 9, invertase, Involucrin, IP-10, Keratins, KGF, Ki67, KOR-SA3544, Kt3 epitope tag, lactate dehydrogenase, Lactoferrin, lactoperoxidase, Lamins, Laminin, La (SS-B), LCMV (Lymphocytic Choriomeningitis Virus), *Legionella pneumophilia* serotype, *Legionella pneumophila* LPS, Leptin and Leptin Receptor, Lewis A Antigen, LH (leutenizing Hormone), LHRH (leutenizing Hormone Releasing), L, (leukemia Inhibitory Factor), 5-Lipoxygenase, LPS Francesella tularensis, luciferase, Cancer Marker (MOC-1, MOC-21, MOC-32, Moc-52), Lymphocytes, lymphotactin, Lysozyme, M13, F1 Filamentous Phages, Macrophages/monocytes, Macrophage Scaveng, Receptor, Matrix metalloproteases, M-CSF, Major Basic Protein, malate dehyrogenase, Maltose Binding Protein, Mannose Receptor (macrophage), Mannose-6-phosphate receptor, MAP kinase antibodies (ERK, ERK, ERK2, ERK3), MASH1 (Mammalian achaete schute homolog 1 and 2), MCL-1, Mcm3, M, (MCAF), MCP-2, MCP-3, Melanocortin Receptors (1 through 5), Met (c-met), Mineralcortocoid Receptor (MR/MCR), Melanoma Associated Antigen, MGMT (methylguanine-DNA-methyltransferase), MHC Antibodies (incl. HLA DATA PACK), Milk F, Globule Membrane, Milk Mucin Core Antigen, MIP-1 alpha, MIP-1 beta, Mitochondrial markers, Mitosin, MMP-1, MM, MMP3, MMP7, MMP8, MMP-9 and MMP13 (matrix metalloproteases), MMP-14(MT1-MM, MMP15 (MT2-MMP), MMP16(MT3-MMP) and MMP19, Morphine, motili, Mucin related antibodies (Muc-1, muc-2, muc-3, muc-Sac), Mucin-6 glycoprotein, Mucin-like Glycoprotein, *Mycobacterium tuberculosis*, Myclin, Myelin Basic Protein, Myeloperoxidase, MyoD, Myoglobin, Myosin, Na+ Ca+ Exchanger Protein, Na+/K+/ATPase, Na+/K+/ATPa, NCAM (CD56), pan N-Cam, (neural cell adhesion marker), Nerve Growth Factor, Neu-Oncogene (c-erb B2), Neurofibrillary Tangle, Neurofilament 70+200 kD, Neurofilament 145 Kd, neurofilament 160 kd, Neurofilament 68 Kd, Neurofilament 200 kd, Neurofilament 200 kd, neurokin, A/substance K, neuromedin U-8 (NMU-8), Neuromodulin, neuronal pentraxin, Neuro-Specific Enolase, Neuropeptide Y (NPY), Neurophysin I (oxytocin precursor), Neurophysin, (vasopressin precursor), Neuropsin, Neurotensin, NFKB, Nicotinic Acetylcholine Receptor, (Beta2 and Alpha 4), NMDA receptors, N-MYC, Norepinephrine Transporter (NET), N, (Nitric Oxide Syntase) eNos, iNos, NT-3, NT, (neurotroph, 4), Nucleolar Helicase, Nucleolar Protein N038, Nuclear Protein xNopp 180, Nucleoplasm, Protein AND-1, Nucleolus Organizing Region (NOR), Nucleolin, occludin, Oncostatin M, ORC, Omithine Decarboxylase, Ovalbumin, Ovarian Carcinoma, Oxytocin, P15, P16, P2, P27, P53 Oncoprotein, p62 Protein, p97 Atpase, membrane associated and cytosolic 42 kDa inositol (1,3,4,5) tetrakisphosphate receptor, PP44 Podocyte Protein (Synaptopodin), PAH (Polyaromatic Hydrocarbons), PACAP (pituitary adenylate cyclase activating peptide), Pancreas Polpeptide (PP), Pancreastatin, Pancreatic Islet Cell, papain, Papillomavirus (HPV), Parainfluenza type 2 viruses, Parathion, Parkin, PARP (Poly-A, Riobose Polymerase) PARP-1 and PARP-2, Patched-1, Patched-2, Paxillin, polychlorinated biphenyls, *Pemphigus vulgaris* (desmoglein 3), Penicillin, penicillinase, pep-carboxylase, pepsin, Peptide YY, Perforin and polyclonals, Perilipin, Peripherin, Perlecan, Petrole, Hydrocarbons (total), PPAR (peroxisome proliferation activated receptors), P-Glycoprotein (multi-drug resistance), PGP9.5, Phenanthrene, Phencyclidine (PCP), Phenylethanolamine, methyltransferase (PNMT), Phospholamban, Phospholipase A2, Phosphoserine, Phosphothreonine, Phosphotyrosine, Phosphothreonine-proline, phosphothreonine-lysi, phophotyrosi, Phosphotyrosine Kinase, *Pichia pastoris*, Placental Alkaline Phosphatase, Plakoglobin, Plakophilin 1, Plakophilin 2, Plakophilin 3, Plasminogen, Platelet Derived Growth Factor AA and BB and AB, Plectin, PM, ATPase (plasma membrane Ca pump), *Pneumocystis carinii*, Pneumolysin, Polychlorobiphenyl (PCB), PP17/TIP47, PPAR (peroxisome proliferation activated receptors), Prednisone, Prednisolone, Pregnancy associated Plasma Protein A (PAPP-A), Pregnenolone, Prepro NPY 68-97, Presenilin-1, Presenilin-2, Prion protein, Progesterone, Progestero, Receptor, Prohibitin, Proinsulin, Prolactin, Proliferation Ce, Nuclear Antigen, Proline Transporter, Prostatic Acid Phosphatase (PAP), Prostatic Specif, Antigen (PSA), Proteasome 26S, Protein 4.1 M ascites, Protein G, Protein Kinase C, *Pseudomonas mallei*, PTH, Pulmonary Surfactant Associated Proteins, Puromycin, Pyruva, kinase, Rabies Virus, RAC-1 and Rac-2, RAGE (receptor for AGE), RANTES, RDX, RecA, Receptor for advanced glycation end products (RAGE), Red Blood cells, Regulatory subunit, RELM alpha and Beta (resistin like molecules), Renin, Rennin, Replication Protein A (RPA p32 and p70), Resistin, Respiratory syncytial virus (RSV), Retinoblastoma (Rb), phospho-specific RB (ser780), Ribonuclease A, RNA Polymera, Arna3, RNP (70KdaU1), A Protein, B Protein, RO (RO52, Ro60), Rotavirus group specific antigen, Rubella virus structural glycoprotein E1, Ryanodine Receptor, S-100 Protein, *saccharomyces cerevisiae*, Salmonella O-antigens, Salmonel, typhimurium, Sarcosine Oxidase, SDF-1 Alpha and SDF-1 Beta, secretin, Selenoprotein P, Serotonin, Serotonin Receptor, Serotonin Transporter, Sex Hormone Binding Globulin (SHBG), SFRP5 (secreted frizzled-related protein 5), SF21 and SF9, SIV gp120, SIV p28, Smooth muscle actin, Somatostatin, *Staphylococcus aureus, Staphylococcus aureus* enterotoxin, STAT1, Stat2, Stat, Stat4, Stat5 Stat6, Stem Cell Factor (SCF) and SCFR/C-kit, Streptavidin, Streptococcus B, Stromal Cell Derived Factor-1 (SDF-I alpha and beta), Substance P, Sufentanil AB, Superoxide Dismutase, Surfactant Associated Proteins (A,B,C,D), Symplekin, Synapsin I, Synapsin Ia, Synaptophysin, Synaptopodin (Podocyte Protein), Syndecan 1, Synphilin-1, Synuclein (alpha), SV40 Large T antigen and small T antigen, Talin, TARC, TAU, Taurine transporter, Tenascin, Testosterone, TGF-alpha, TGF-beta, TGF beta receptor (Endoglin), THC, Thomsen Friedenreich Antigen (TF), THY-1 25 kd Brain (CDw90), Thymocytes, Thrombin and Thrombin Receptor, Thyroglobulin (24TG/5E6 and 24Tg/5F9), Thyroid Binding Globulin, Thyroid Hormone Receptors, Thyroid Peroxidase, Thyroid Stimulating Hormone (TSH), Tyrosine Hydroxylase, Thyrotropin Releasing Hormone (TRH), Thyroxine (T4), Tle-1 and Tle-2, TIMP-1, TIMP-2, TIMP-3 (Tissue Inhibitors, metalloproteinase), Titin, TNF receptor associated factors 1 and 2, TNF Receptor, TNF receptor II, TNF-Alpha, TNF-Alpha, TNF-beta, *Toxoplasma gondii* p30 antigen, TPO (thrombopoietin), TRAF, Traf2, Traf3,TRAF4,TRAF5, TRAF6, Transferrin, Transferrin Receptor, Transforming Growth Factor A, Transformi, Growth Factor Beta, Transportin, Trepone, pallidium, Triiodothyronine (T3), Trinitrotoluene (TNT), TRK A, TRK B, TRK C, Tropon, (cardiac), Troponin I, Troponin T, trypsin, trypsin inhibitor, trypsinogen, TSH, TUB Gene, Tubulin alpha and beta, Tubulin beta specific, Tumor Marker related Antibodies, Tumor Necrosis Factor Alpha, Tyrosinase, Tweak, (caspase-4), Ubiquitin, Ubiquitin-L1, Uncoupling Proteins (UCP1, UCP2, UCP3, UCP 4 and UCP5), Urease, Uricase, Urocortin, Uroplakin, Vasopressin, Vasopressin Receptor, VEGF, Vesicular acetycholine transport, (VACht), Vesicular monoamine transporter (VMAT2), Villin, Vimentin, Vinculin, VIP (Vasoactive Intestinal Peptide), Vitamin B 12, Vitamin B 12, Vitamin D metabolites, Vitamin D3 Receptor, Von Willebrand Factor, VSV-G Epitope Tag, Wilm's tumor Protein X, Oxida, Yeast, hexokinase, SOD, cytochrome oxidase, carboxypeptidase, and *Yersinia eterocolotica*. Incorporating any such antibody is generally a matter of either mixing a solution of the antibody into the liquid crystal (or, preferably, use the antibody solution as the aqueous material in the preparation of the composition corresponding to the liquid crystal), or incubating a material or particle dispersion with the antibody solution. For example, if a reversed cubic or hexagonal phase exists in equilibrium with excess water (or other polar solvent or polar solvent mixture), then the antibody solution can be contacted with a film of the liquid crystalline material for a period of time to allow the antibody to diffuse into the liquid crystal. The same methodologies can be applied for the incorporation of a wide range of bioactive compounds and macromolecules in particular.

Alternatively, many of the substances noted in the above list (e.g. folate, PGP, cytochrome P 450, and EGF) may in and of themselves be useful as targeting substances and may be incorporated into the particles of the present invention. In addition, other chemical compounds such as PEG may also be used for targeting and may be incorporated.

It is important to point out that in addition to targeting compounds per se, active compounds, functional excipients such as absorption enhancers, and other bioactive materials as gleaned from the lists of materials given herein can be incorporated. Of particular interest are inhibitors of efflux proteins, such as P-glycoprotein.

Certain oils and (mixtures of) hydrophobes are themselves functional excipients, that is, bioactive in themselves beyond the more passive functions associated with many pharmaceutical excipients. For example, certain essential oils that can be incorporated into, or serve as the main component of, first volumes of the instant invention are known to be P-glycoprotein inhibitors. These include the following essential oils or components thereof: santalwood, cedarwood, patchouli, peppermint, carrot see, cloves, ylang-ylang, fir needle, mugwort, oregano, Roman chamomile, eucalyptus, ginger, thuja, hyssop, and myrrh. Lipids are also in many cases functional excipients and therefore bioactive. For example, in one embodiment of this invention, the bioactive agent dissolved or dispersed in the first liquid phase is a nucleic acid and the bioactive agent in the second liquid crystalline phase is a tranfection-promoting agent such as Lipofectamine.

Furthermore, liquid crystalline phases themselves can in many cases be "bioactive", in a sense beyond the sum of the effects of the individual components, by virtue of their morphologies and phase behavior. In particular, reversed cubic and hexagonal phases often exhibit fusogenic tendencies that can play a crucial role in enhancing drug uptake by increasing permeability across absorption barriers, both transcellular and pericellular, as has been mentioned several times in this text.

In addition to the targeting of particles to specific sites for release of drug, as mentioned above particles incorporating certain radiopaque or optically dense materials could themselves be used for imaging, and when coupled to targeting compounds as described herein could target specific sites in the body and allow their visualization. As an example, somatostatin receptors are known to be localized at certain tumor sites, so that the attachment of a target to coated particles as per the instant invention that would bind selectively to somatostatin receptors could target a tumor and allow visualization via, e.g., x-ray, MR imaging, or radioimaging. To extend this idea, a similarly targeted particle could then carry a radioactive material that would emit radiation intended to induce necrosis of the tumor.

In the utilization of particles of this invention in general, but particularly in the context of particle targeting, the second volume can play a number of roles in the application of these materials: enhancing absorption by virtue of surfactancy and/or interactions with biomembranes; solubilizing and then releasing absorption enhancers (e.g., gum benzoin), acids, bases, buffers, specific ions (e.g., manganese in the case where lectin binding is important), modulators of protein binding or activity, or other bioactive materials; and providing a matrix ensuring the proper presentation of molecular recognition sites.

Agricultural uses are within the scope of use of the instant invention, including direct application of particles or materials of the invention to plants. Dispersions could be sprayed on leaves using ordinary crop-dusting technology, for example, delivering fertilizers, pesticides, nucleic acids, proteins, peptide, growth factors, or hormones.

It is also within the scope of this invention to create materials or particles in which two hydrophobe-rich liquids form distinct pockets within the liquid crystal volume. Not all hydrophobes are mutually miscible. For example, simethicone and vegetable oil are poorly miscible. Therefore, applying the techniques described herein with these two hydrophobes instead of one would result in separate pockets of the two substances, provided that the equilibria requirements discussed herein apply.

Application of the Materials and Particles.

The particles 1 of the present have application in a variety of fields. The particles 1 are adapted to release one or more materials, such as active agents, disposed in the first volume 10.

With respect to release, the particles may be used for the controlled release of pharmaceutical agents, such as anticancer agents or photodynamic therapy agents, or cosmetic or cosmeceutical materials. An active agent may be disposed in the first volume 10 for release upon the triggering of release. For example, a pharmaceutical or biologically active material may be disposed in the first volume. Particles and materials of this invention can be used for many routes of adminstration including parenteral (intravenous, subcutaneous, and intramuscular in particular), oral, intraperitoneal, topical, transdermal, buccal, rectal, otic, occular, nasal, and sublingual. Upon administration of the particle, typically via oral, intraperitoneal, or injectable route, or of a contiguous material, typically by topical application (e.g., for transdermal delivery) containing an active, the solubilization of the active will circumvent dissolution-limited absorption, the presence of the nanoporous liquid crystal can enhance interactions with membranes thereby improving uptake via transcellular or pericellular transport, and/or the physicochemical properties of the liquid crystal can release the active at a rate, or according to a profile, that is desirable or even preselected.

For oral administration of an active, three general approaches for applying the present invention are:

1) filling a capsule with one or more aliquots of a contiguous material; in this case the contiguous second volume can provide a high-viscosity matrix useful for compatibility with certain filling procedures and requirements, in addition to the desirable features listed above;

2) filling a capsule with a dispersion of particles of the instant invention; and 3) coating the particles according to techniques described or referenced herein, and then applying solids-handling techniques that are well-known in the art of solid dosage forms.

For administration by injection, dispersions of particles of the instant invention, in some cases with a solid coating applied as discussed herein, can be injected provided the particle size is small enough (typically less than 200 nm for intravenous injection, or larger for subcutaneous or intramuscular); usually the exterior phase in which the particles are dispersed would be an aqueous solution (usually with adjusted osmolarity), though oil-rich exterior phases can also be contemplated.

For topical administration, any of the above formats could be applied, though the contiguous material would be most likely to be of value. In cases where a dispersion was desired, a more viscous exterior phase would normally be used, such as glycerol, a viscous oil, or an aqueous phase with appropriate thickeners.

Particles or materials of the present invention can be used to control the release of an active, according to a number of scenarios which can be substantially preselected. To begin with, if the components of the material or particle are chosen with proper attention to the partition coefficient of the active, then the active can be made to release at a slower rate due to partitioning into the particle or material. Similar effects can also be obtained by the judicious use of charged membrane components in the liquid crystal. For larger actives, particularly proteins, nucleic acids (e.g., antisense compounds), antibodies, polysaccharides, and other biomacromolecules or biopharmaceuticals, a powerful approach can be to dispose these into a polar-solvent first volume and then use the controlled porosity of the second volume to control release of the active. Furthermore, a crucial aspect of such an approach is that the pores of the liquid crystal can provide a means by which to limit access to the active by offensive macromolecules such as proteases, nucleases, enzymes and other entities—including various cell types, for example—that would otherwise degrade or sequester the active. In addition, solid coatings can be applied (as discussed herein) to provide another powerful feature for controlling release and/or preventing release until certain conditions (e.g., pH, enzymatic action, etc.) trigger the release of the coating. Going in the other direction, if release and/or absorption of the active is normally retarded by solubility limits, precipitation, or poor interactions with biomembranes, then particles of the instant invention can serve the role of accelerating release and/or uptake.

In applications of these microparticles in drug-delivery or with embedded proteins or polypeptides (in particular receptor proteins), it can be highly advantageous to have a second volume which, although synthetic or semisynthetic, is designed to simulate closely the physiochemical properties of a natural biomembrane from a living cell. This could be important for the proper functioning of a receptor protein or other membrane component, for example, or for promoting assimilation of the second volume into the natural biomembrane in drug-delivery. Physiochemical properties that can be important in such a context include the bilayer rigidity (a measure of the resistance to bending), bilayer fluidity (a measure of the microviscosity of the bilayer interior), the acyl chain length and bilayer thickness, the order parameter as a function of position on the lipid acyl chains, the surface charge density, the presence or absence of segregated lipid domains of differing composition within the bilayer, bilayer curvature and monolayer curvature (for a discussion of the relationship between these two curvatures see H. Wennerstrom and D. M. Anderson, in Statistical Thermodynamics and Differential Geometry of Microstructured Materials, Eds. H. T. Davis and J. C. C. Nitsche, Springer-Verlag, 1992, p. 137), cholesterol content, carbohydrate content, and the lipid:protein ratio. By proper choice of composition, one can adjust these parameters to a large extent in an artificial system, namely a nanostructured nonlamellar liquid crystalline phase. For example, the bilayer rigidity can be reduced by the addition of amphiphiles, particularly aliphatic alcohols; and bilayer charge can be adjusted by adjusting the ratio between uncharged lipids (such as phosphatidylcholine) and charged lipids (such as phosphatidic acid). Also, the addition of cholesterol is important for the function of a number of membrane proteins. The lamellar phase, the reversed bicontinuous cubic phase, the L3 phase, and to a lesser extent the reversed hexagonal phase are in particular well-suited for this approach. Thus, a particle of the present invention, with the second volume being such a phase with tuned physiochemical characteristics for the functioning of incorporated proteins or other biomolecules, can be very valuable in products for pharmaceutics, clinical assays, biochemical research products, etc.

Membrane proteins are generally dependent on a bilayer milieu in order to function properly and even to maintain proper conformation, and for such proteins the present invention—B particularly with the bilayer properties tuned as described above—could be an excellent and very useful second volume. Examples of membrane proteins include, in addition to receptor proteins, such proteins as proteinase A, amyloglucosidase, enkephalinase, dipeptidyl peptidase IV, gamma-glutamyl transferase, galactosidase, neuraminidase, alpha-mannosidase, cholinesterase, arylamidase, surfactin, ferrochelatase, spiralin, penicillin-binding proteins, microsomal glycotransferases, kinases, bacterial outer membrane proteins, and histocompatibility antigens.

We note that the current invention is also very well suited for the incorporation of functional excipients, such as gum benzoin or essential oils that improve absorption of poorly-absorbed drugs, in some cases by inhibiting drug efflux proteins.

Other examples of uses of particles of the present invention include:

1. Paints and inks, including Microencapsulation of pigments; Cationic charging of pigments (where pH-dependence can be important); Fillers and texturizing agents for non-aqueous paints;
2. Paper, including Microcapsular opacifiers (also in paints); Pressure-sensitive ink microcapsules for carbonless copying paper;
3. Non-wovens, including Additives that adhere to fibers throughout processing;

4. Agricultural, including Controlled release of pheromones (some of which are otherwise volatile or environmentally unstable if not encapsulated) for insect control; Controlled release of insect chemosterilants and growth regulators (many of which are otherwise environmentally unstable); Controlled release of other pesticides (with temperature independence being important); Controlled release of herbicides; Encapsulation of the plant growth regulators ethylene and acetylene (that are otherwise volatile); Taste modifiers to deter mammalian pests (e.g., capsaicin); Nutrient and fertilizer release;

5. Environment and forestry, including Controlled release of aquatic herbicides for weed control; Controlled release of other herbicides; Controlled release of nutrients in mariculture; Soil treatment and nutrient release; Encapsulation and release of chelating agents (e.g., for heavy metal contaminants); Control of deposition and environmental fate of actives (viz., through targeted release of crystal coating and/or adhesive property of cubic phase); Encapsulation of hygroscopic or other (e.g., urea and sodium chloride) "seeding" agents for meteorological control;

6. Vaccines, including HIV gag, gag-pol transfection of cells as an example; Adjuvants for the proper presentation of antigens or antibodies;

7. Nuclear medicine, including Separation of two (otherwise mutually-destructive) radionuclides into separate particles for treatment of cancer;

8. Veterinary, including Controlled release of volatile anti-flea compounds; Encapsulated feed additives for ruminants; Encapsulation of anti-microbial and insecticides in animal husbandry;

9. Dental, including Controlled-release dentifrice components, particularly hydrolytically unstable anti-calculus compounds; Delivery of oral anti-cancer compounds (photophyrin);

10. Polymerization catalysts or crosslinkers in one-pot (single-package) resin systems;

11. Household products, including Controlled-release air fresheners, perfumes; Controlled-release insect repellants; Laundry detergents (e.g., encapsulated proteases); Other detergency applications; Softeners; Fluorescent brighteners;

12. Industrial, including Encapsulation of phosphine, ethylene dibromide, etc. volatiles for fumigating stored products; Catalytic particles; Activated charcoal microparticles for sorption and purification;

13. Polymer additives, including Polymer additives for protection of wires, paper cartons etc. from rodents; Impact modifiers; Colorants and opacifiers; Flame retardant and smoke suppressants; Stabilizers; Optical brighteners;

14. Food and beverage processing, including Encapsulation of (volatile) flavors, aromas, and oils (e.g., coconut, peppermint); Encapsulation of vegetable fats in cattle feeds; Encapsulated enzymes for fermentation and purification (e.g., diacetyl reductase in beer brewing); Encapsulation as an alternative to blanching, for improved lifetime of frozen foods; Microencapsulated tobacco additives (flavorings); pH-triggered buffering agents; Removal of impurities and decolorization using activated charcoal encapsulated in a porous material;

15. Photographics, including Fine-grain film with dispersions of submicron photoreactive particles; Faster film due to optical clarity (and thus higher transmission) and shorter diffusion times of submicron dispersion; Microencapsulation of photoprocessing agents;

16. Explosives and propellants, including Both liquid and solid propellants and explosives are used in encapsulated form; also, water is used in encapsulated form as a temperature moderator in solid propellants;

17. Research, including Microcapsule-packed columns in extractions and separations; Biochemical assays, particularly in pharmaceutical research and screening;

18. Diagnostics, including Encapsulated markers for angiography and radiography and Clinical assays involving milieu-sensitive proteins and glycolipids.

Polymerized Liquid Crystals.

U.S. Pat. No. 5,244,799 (the contents of which are hereby incorporated by reference in entirety) reports the polymerization of nanostructured cubic and hexagonal phase liquid crystals, with retention of their nanostructure. The retention of structure was demonstrated by small-angle x-ray scattering (SAXS) and transmission electron microscopy (TEM).

The possibility of polymerizing the second volume of a particle of the instant invention opens up a number of possibilities, particularly as relate to increasing the stability of the second volume, immobilizing a targeting compound, preventing changes in its poresize, and modulating its interaction with the body, and cell membranes in particular. For an example of the latter, whereas an unpolymerized cubic phase might be expected to molecularly disperse when coming into contact with a biomembrane, polymerization of the same second phase might create a particle interior that would retain its integrity throughout its interaction with the same biomembrane, and this could have dramatic consequences as to the fate of the particle and to a drug inside the particle. For the case of a second volume that contains a targeting compound (such as an antibody, receptor, lectin, complementary nucleic acid, etc.), polymerization of this second volume can provide a means by which to retain the target, even in the face of large volumes of body fluids, etc. Furthermore, the retention of a bilayer-bound drug (hydrophobic small molecule, membrane protein, etc.) might be increased tremendously by polymerization, yielding a slow-release particle. And the presence of a more permanent, precisely-defined pore structure, with precisely tunable poresize, might make possible improved controlled release of a drug, and/or sequestration of the drug from degradative or other enzymes by size-exclusion from the pores of the polymerized matrix.

Methods of Producing Materials and Particles of the Invention.

In a preferred embodiment, the various means for producing particles of the type disclosed herein may be divided into two classes, which may be referred to as Type I and Type II Processes. It is important to note that in the case where particles with a hydrophobic first volume are to be dispersed in a polar solvent, or particles with a polar solvent first volume are to be dispersed in a hydrophobic liquid, then the amphiphilic nature of the liquid crystalline phase makes the second volume naturally predisposed to situate between the two immiscible liquids; the same is true for the case where the polar solvent and hydrophobic liquid are interchanged. This is a crucial aspect of the invention which provides for simple production methodologies for producing particles in which the first volume is enclosed by the second volume, since thermodynamics will favor the situation where contact between the first volume and the exterior phase (in which the particles are dispersed) is prevented by the second volume enclosing the first volume.

Type I Process.

In this type of process, the particles are formed in aqueous dispersion, or more generally, dispersed in a polar solvent or mixture of polar solvents; or, the roles of polar and apolar solvents are reversed, and particles are formed in a dispersion where the continuous phase is a hydrophobe-rich liquid; alternatively, a variation of this method produces materials in which the non-lamellar liquid crystal is the continuous phase. Typically, the polar solvent or mixture (or hydrophobe-rich mixture, depending on which polarity the first volume is), with active dissolved, is combined with a lyotropic liquid crystal or precursor (e.g., dehydrated variant) thereof and the water-immiscible (or polar liquid) exterior phase overlain, and energy applied to disperse the liquid crystal, often in the presence of a surfactant or other stabilizer. Methods to apply the energy include sonication, vigorous stirring or pumping, high-pressure homogenization, and other methods commonly applied in homogenization processes.

In more detail, the starting point for a Type I process is a three-phase region of equilibrium between the first and second volumes and the exterior phase in which the particles are dispersed. This is typically determined by mapping out the phase behavior of a ternary (or pseudternary) system containing the polar solvent (usually water), hydrophobe (or hydrophobic liquid, perhaps a mixture of hydrophobes), and lipid or surfactant. The various liquid crystalline phases are identified according to the methods and criteria discussed above. For the Examples given herein, most of these liquid crystals were determined by a combination of polarizing optical microscopy and small-angle x-ray scattering.

The addition of the active solubilized in hydrophobic solvent (or polar solvent) can be performed preferably prior to this dispersing step, or added gradually after a significant fraction of the dispersing step has been performed. Energy input continues then, whereby the hydrophobe-active solution is dispersed into the interiors of the particles. Alternatively, application of energy to a physical mixture of two phases in equilibrium, one being the nonlamellar liquid crystal and the other being the desired liquid phase, can produce a material of the present invention in which pockets of the liquid phase are dispersed in the nonlamellar liquid crystalline material; this approach requires that a two-phase equilibrium exist between the liquid and nonlamellar liquid crystalline phases.

Dispersions of particles of the present invention in a liquid (polar or hydrophobic) can be created in a number of ways. A good starting point is to mix a composition that lies in a two-phase region in which the first and second volumes are in equilibrium (the active being predissolved in the solvent of the first volume). This two-phase region should also be selected such that the addition of the exterior phase will yield a composition that lies in a three-phase region where the first volume, second volume, and exterior phase are in equilibrium with each other. While centrifugation is useful in determining that the two phases are in equilibrium, and in determining their compositions, in such a production process one would generally want to avoid centrifuging, and rather let the two phases intermingle. The exterior phase is then added, and energy input is applied by one or more of a number of available homogenization techniques, such as sonication, or a standard homogenizer.

In addition to sonication and homogenization, other standard emulsification methods could be used as energy inputs. These include microfluidization, valve homogenization, blade stirring, etc. Desirably, a surfactant, such as an ionic surfactant or an amphiphilic block copolymer of several thousand Dalton molecular weight, is added to the aqueous solution in order to stabilize the particles against aggregation as they form. The surfactant is generally chosen so that it is more soluble in the exterior phase than in the first volume. If sonication is used to promote particle formation, this surfactant also serves to enhance the effect of sonication. As stated elsewhere herein, thermodynamics works in favor of forming multicompartmental particles in which unfavorable contact between hydrophobe-rich and polar solvent-rich phases (i.e., the first volume and the exterior phase) is limited or prevented by the enclosure of the first volume by the amphiphilic liquid crystalline phase second volume.

In addition to traditional surfactants, it has been found that salts of certain ionizable hydrophobic materials, such as the amino acid tryptophan or its N-acetyl derivative, can be used to disperse certain liquid crystals (including a cubic phase in the soy phosphatidylcholine (Epikuron 200, from Lucas-Meyer)/tryptophan/water system), and that energy input requirements can be extremely low with this choice of components Particles of reversed cubic or hexagonal phase can also be dispersed in water by, for example, techniques described in U.S. Pat. No. 5,531,925. In that patent, the entirety of which is incorporated by way of reference, liquid L3 phases were used to disperse reversed cubic phases. Such techniques apply in the case of hydrophobic-core particles of the instant invention, bearing in mind that the requirement of four-phase equilibrium (first volume, second volume, L3 phase, and exterior water phase) that this engenders requires at least four components, by application of the Phase Rule. Preferably, these four components would be the hydrophobe, water, a water-insoluble lipid or surfactant, and a water-soluble polymeric surfactant such as a Pluronic (e.g., Pluronic F-68).

Type II Processes. In the preferred form of this type of process, spray-drying, spray-congealing, or similar process is used to form particles from, preferably, spraying a single-phase liquid at elevated temperature (generally between 40 and 120° C.), wherein this hot liquid phase separates upon cooling to a liquid crystalline phase and a hydrophobe-rich phase. Because of the presence of substantial amounts of surfactant or lipid and of hydrophobic solvent(s), one can reasonably expect that a number of two-phase systems as described above (in which a liquid crystalline phase is in equilibrium with a hydrophobe-rich phase) will exist as hot liquids at some elevated temperature less than 120° C. In such cases, feeding this single-phase liquid into a spray-drying apparatus will result in droplets that, as they cool in flight and afterward, will change from hot liquid droplets to particles comprising liquid crystalline and hydrophobe-rich phases. In some such cases, surface energies will promote the coating of the hydrophobe-rich (or polar, depending on the desired core) phase with the liquid crystalline phase. If a precursor to a solid material is also present in the melt, it can result in particles with a liquid first volume, a liquid crystalline second volume outside that, and an outermost solid shell. In this latter case, there need not necessarily be any requirement for the two phases to be in equilibrium with a polar solvent (or mixture of polar solvents).

The following examples illustrate the present invention but are not to be construed as limiting the invention.

EXAMPLES

Example 1

Essential oil of sweet basil, in the amount of 0.827 grams, was mixed with 0.765 gm. of the water-insoluble surfactant Tween 85 (available from Aldrich), 0.395 gm. of alpha-tocopherol, and 0.955 gm. water, and the mixture centrifuged for 16 hours in a table-top centrifuge (on the order of 3,000 G). At that time a basil oil-rich top phase had separated out which was decanted. A Tween-rich middle layer containing a reversed-type liquid crystalline phase was present as well as a bottom aqueous phase. About 4 ml. of water was added to the middle and bottom layers and this mixture sonicated using a DENEX ultrasonic cleaner, forming a crude dispersion. Estradiol (available from Sigma), in the amount of 15 mg., was dissolved in 0.594 gm. of the basil oil-rich top phase, and the following were overlaid on this solution: 2.463 gm. of the crude dispersion, 2.452 gm. of water, 18 mg. of sodium taurocholate (available from Aldrich)and 28 mg. of Pluronic F-68 (available from BASF). The mixture was then sonicated, yielding microdroplets having an estradiol-containing basil-rich core, coated by a reversed liquid crystalline material. Concerning the low toxicity and approval status of the components used in this formulation, Tween 85 is approved for use not only in oral drug formulations but also for injectable formulations; alpha-tocopherol (vitamin E) is present in a side range of formulations including oral and injectable; oil of basil is a Generally Recognized As Safe (GRAS) oil that is approved for use in oral formulations, and belongs to a family of essential oils that exhibit anticancer activity in themselves.

Example 2

Essential oil of peppermint, in the amount of 0.748 grams, was mixed with 0.625 gm. of the surfactant BRIJ 76 (main component: decaethylene glycol octadecyl ether) (available from Aldrich), 0.244 gm. of alpha-tocopherol, and 0.679 gm. water. The mixture centrifuged for 16 hours in a table-top centrifuge (on the order of 3,000 G) at which time a peppermint oil-rich top phase had separated out which was decanted. A BRIJ-rich middle layer containing a reversed-type cubic phase liquid crystal was present, containing excess water. About 4 ml. of water was added to the BRIJ-rich layer and this mixture sonicated, forming a crude dispersion. Paclitaxel, in the amount of 6 mg. was dissolved in 0.147 gm of the peppermint oil-rich top phase, and the following were overlaid on this solution: 0.479 gm. of the crude dispersion, 0.352 gm. of water, 4 mg. of sodium taurocholate and 5 mg. of Pluronic F-68 (available from BASF). The mixture was then sonicated as above in Example 1, yielding microdroplets having a paclitaxel-containing peppermint-rich core, coated by a reversed cubic phase liquid crystalline material. All of the components used in this formulation are of very low toxicity and approved or approvable for use in oral formulations.

Example 3

A crude dispersion of similar composition to that of Example 1 was prepared as follows. Essential oil of sweet basil, in the amount of 1.644 grams, was mixed with 1.529 gm. of Tween 85 (available from Aldrich), 0.798 gm. of alpha-tocopherol, and 1.941 gm. water, and the mixture centrifuged for 16 hours in a table-top centrifuge (on the order of 3,000 G). A basil oil-rich top phase had separated out which was decanted. A Tween-rich middle layer containing a reversed-type liquid crystal was present as well as a bottom aqueous phase. Water, 5.05 gm., 0.074 gm. of sodium taurocholate, and 0.044 gm. of Pluronic F-68, were added to the middle and bottom layers and this mixture sonicated, forming a crude dispersion. Manadione (Vitamin K2) (available from Sigma), in the amount of 40 mg. was dissolved in 0.372 gm. of the basil oil-rich top phase, and the following were overlaid on this solution: 2.062 gm. of the crude dispersion, and 1.101 gm. of water. The mixture was then sonicated, yielding microdroplets having an manadione-containing basil-rich core, coated by a reversed liquid crystalline material.

Example 4

The surfactant Tween 85 (Polysorbate 85), in the amount of 0.361 grams, was combined with 0.084gm of the preanesthetic agent Propofol (Diprovan), 0.145 gm of gentisic acid ethanolamine, 0.172 gm of alpha-tocopherol, and 0.201 gm water. Upon centrifugation, a Propofol-rich top layer separated out atop a layer containing a reversed liquid crystalline phase. Approximately 3 ml of water was then overlaid and the mixture sonicated, resulting in a dispersion of microparticles containing a Propofol-rich core coated by a reversed liquid crystalline phase.

In related experiments, Propofol was replaced by a mixture of Propofol and eugenol, and after dispersing, the dispersion was combined with a solution of dextrose and calcium hydroxide in water. Whereas Propofol does not react significantly with calcium hydroxide under these conditions, eugenol does, forming the calcium salt of eugenol on the particles. Such a coating can be useful in limiting microbial growth that is a problem with current Propofol formulations.

Example 5

The surfactant Tween 85 (Polysorbate 85), in the amount 0.916 gm, was combined with 0.173 gm Propofol, 0.324 gm of water, and 0.024 gm of L-tryptophan. Upon mixing and centrifuging, a Propofol-rich top phase separated out, as well as excess tryptophan on the bottom, and the middle layer contained a reversed liquid crystalline phase. Approximately 4 ml of water was added to half of this mixture, and the combined system sonicated, resulting in microparticles with a Propofol-rich core coated by a reversed liquid crystalline phase.

It is apparent that many modifications and variations of the invention may be made without departing from the spirit and scope of the present invention. It is understood that the invention is not confined to the particular construction and arrangement herein described, but embraces such modified forms of it as come within the appended claims. The specific embodiments described are given by way of example only and the invention is limited only by the terms of the appended claims.

Example 6

The surfactant "Ethox 2984" from Ethox Corporation, whose main component is stearyldiethanolamide, in the amount of 0.42 grams, was mixed with 0.01 grams of progesterone dissolved in 0.42 grams of oil of peppermint, 0.18 grams of alpha-tocopherol, and 0.3 grams of water. This composition formed a two-phase mixture of a reversed cubic phase and excess oil-rich phase, as indicated by polarizing optical microscopy examination; the same mixture without the tocopherol resulted in a multiphase sample with textures indicating the presence of a lamellar phase. A solution of 0.08 grams of sodium docusate in 15 ml of water was overlaid on the tocopherol-containing sample, and the mixture sonicated. This dispersion was then subjected to further particle size reduction in a Model 110S Microfluidizer, applying approximately 20 piston strokes using 50 psi air pressure. This Microfluidizer amplifies the input pressure by a factor of 220, meaning that the pressure on the fluid in this homogenization step was approximately 11,000 psi. The resulting dispersion consisted of submicron particles almost entirely, with essentially nothing larger than one micron evidenced in the optical microscope, and no evidence of oil exterior to the microparticles.

Example 7

A mixture of essential oils of thyme and peppermint (from Aura Casia), at a ratio of 2:1 by weight thyme:peppermint, was first prepared. To 2.0 grams of this mixture were added 2.0 grams of Pluronic P103 surfactant and 20.0 grams of distilled water. Pluronic 103 is a polypropyleneoxide-polyethyleneoxide block copolymer surfactant from BASF. Previous experiments showed that a cubic phase forms with P103 combined with the thyme:peppermint oils in excess water. This mixture was first sonicated, and then further particle size reduction was accomplished by subjecting the sonicated dispersion to microfluidization, using a Model 110S Microfluidizer from Microfluidics. Air pressure was set at 80 psi, with a 75 micron interaction chamber in place. The microfluidization was carried out for 10 seconds (20 strokes of the piston). The dispersion was then examined in an optical microscope and seen to have a particle size distribution consisting mainly of submicron particles, together with a minority population of particles in the 1–5 micron range. Those particles which were large enough to see in detail showed a multicompartmental structure consistent with an oil-core particle structure; there was no visual evidence of oil domains lying outside the microparticles, nor did centrifugation (3,000 RCF) produce any macroscopic oil-rich phase. The thyme:peppermint oil mixture has been shown by the present inventor to dissolve an investigational antibiotic from Antex Biologics Corporation known as "AP-41", which is an insoluble benzodiazepam compound.

Example 8

The Lucas-Meyer product "Epikuron 145", a moderate-purity soy lecithin, in the amount of 1.49 grams, was combined with 1.51 grams of a 2:1 (by weight) mixture of essential oils of thyme and peppermint, 25.0 grams of a 2:1 mixture of water and glycerol, and 0.13 grams of sodium dodecyl sulfate. This was dispersed by sonication, to produce microparticles with an oil-core of thyme-peppermint oil. Following this, further particle size reduction was accomplished by subjecting the sonicated dispersion to microfluidization, using a Model 110S Microfluidizer from Microfluidics. Air pressure was set at 40 psi, with a 75 micron interaction chamber in place. The microfluidization was carried out for 20 seconds (about 20 strokes of the piston). The dispersion was then examined in an optical microscope and seen to have a particle size distribution consisting mainly of submicron particles, together with a minority population of particles in the 1–5 micron range.

Example 9

The rhamnolipid product "JBR-599" was purchased from Jeneil Biosurfactant Company. This lipid, in the amount of 1.0 grams, was combined with 20 grams water and 1.0 grams of a 1 wt % solution, in a 2:1 mixture of oil of thyme and oil of peppermint, of the steroidal drug progesterone. This mixture was sonicated to produce a dispersion of microparticles, which also contained a modest fraction of supermicron particles. The oil-core structure of the larger particles was clearly visible in the optical microscope.

Example 10

Streptomycin suulfate, in the amount of 20 mg, was dissolved in 0.980 gm of water along with 1 mg of dextran blue as a marker. Of this solution, 0.409 gm was combined with 0.255 gm of phosphatidylcholine-rich "Epikuron 200" (from Lucas-Meyer) and 0.202 gm of essential oil of red thyme (which has as main component thymol, an excipient which is approved for use in pharmaceutical formulations via oral and inhalation routes). This mixture contained a reversed cubic phase liquid crystal. To this were overlain 3.82 gm of more oil of thyme, together with 0.030 gm of the surfactant Pluronic F-68, and the mixture sonicated. Microparticles of the instant invention were formed, with water-rich microdroplets enclosed by reversed cubic phase.

Example 11

A 1.9% aqueous solution of the cosmetic ingredient Allura Red was first prepared. Of this solution, 0.563 gm was combined with 0.556 gm of the ethoxylated, hydrogenated castor oil surfactant Arlatone G (Uniquema), and 0.416 gm of essential oil of ginger (ginger fluid extract is an excipient which is approved for use in pharmaceutical formulations via the oral route). This mixture contained a reversed cubic phase liquid crystal, together with excess aqueous solution. This mixture was then dispersed, using sonication, into 4.376 gm of flavonone had been melted by heating to 60° C. Upon cooling, this fat then formed a solid in which particles of the current invention-with strongly-colored aqueous droplets enclosed by a reversed cubic phase-were entrapped. Milling this material resulted in particles, that is, solid particles in turn containing the liquid/liquid crystalline particles of the present invention.

Example 12

In this Example a blue-labeled, high-MW protein, myosin fluorescent marker (Sigma, product #M-0163), in the amount of 4 mg, was dissolved in 0.126 gm water, add 0.061 essential oil of spearmint, 0.078 gm Epikuron 200 were stirred. The resulting material contained a reversed cubic phase and excess aqueous protein solution. To this were 1.159 gm of oil of spearmint, and this was sonicated, creating microparticles in which the cubic phase enclosed microdroplets of the protein-laden aqueous phase. These particles were seen to exhibit a blue color in optical microscopy (400×), against a colorless background.

I claim:
1. A particle or material comprising
a distinct nanostructured nonlamellar liquid crystalline material; and one or more pockets or droplets of a liquid phase embedded within said distinct nanostructured nonlamellar liquid crystalline material, said liquid phase being selected from the group consisting of an oil-rich liquid phase and a polar solvent-rich liquid phase.
2. The particle or material of claim 1 wherein said distinct nanostructured nonlamellar liquid crystalline material is a reversed phase nonlamellar liquid crystalline material.
3. The particle or material of claim 1 wherein said distinct nanostructured nonlamellar liquid crystalline material comprises
a reversed hexagonal phase material,
a reversed bicontinuous cubic phase material,
a reversed discrete cubic phase material, or
a reversed intermediate phase material.

4. The particle or material of claim 1 wherein said distinct nanostructured nonlamellar liquid crystalline material is polymerized.

5. The particle or material of claim 1 further comprising a stabilizing layer exterior to said particle or material.

6. The particle or material of claim 5, wherein said stabilizing layer is selected from the group consisting of a charged moiety, a polymer, and a surfactant.

7. The particle or material of claim 1, wherein said particle or material further comprises a coating.

8. The particle or material of claim 1 wherein said liquid phase is an oil and said oil is selected from the group consisting of benzyl benzoate, estragole, eugenol, isoeugenol, linalool, and the essential oils of basil, bay, bois de rose (rosewood), carrot seed, clovebud, eucalyptus, ginger, grapefruit, hyssop, lemon, balsam of Peru, mugwort, myrrh gum, bitter orange, oregano, palmarosa, patchouly, peppermint, petitgrain, rosemary, santalwood oil, spearmint, thuja (cedar leaf), thyme, vanilla, and ylang ylang (cananga).

9. The particle or material of claim 1 wherein said liquid phase is a polar solvent and said polar solvent is selected from the group consisting of water, glycerol, and N,N-dimethylacetamide.

10. The particle or material of claim 1 wherein said particle or material is pharmaceutically acceptable.

11. The particle or material of claim 10 wherein said particle or material is pharmaceutically acceptable for injection.

12. The particle or material of claim 11 wherein said particle or material is pharmaceutically acceptable for oral delivery.

13. The particle or material of claim 1, wherein said one or more pockets or droplets have a diameter of 50 nm or greater.

14. The particle or material of claim 1, wherein said liquid phase includes at least one of an oil and a polar solvent.

15. The particle or material of claim 1, wherein said liquid phase is a hydrophobe-rich phase or a polar solvent-rich phase.

16. The particle or material of claim 1 wherein said distinct nanostructured nonlamellar liquid crystalline material consists essentially of a reversed bicontinuous cubic phase material.

17. The particle or material of claim 1 wherein said distinct nanostructured nonlamellar liquid crystalline material consists essentially of a reversed discrete cubic phase material.

18. The particle or material of claim 1 wherein said distinct nanostructured nonlamellar liquid crystalline material comprises a water insoluble lipid or surfactant.

19. A particle or material consisting essentially of,
a distinct nanostructured nonlamellar liquid crystalline material; and one or more pockets or droplets of at least one liquid phase embedded within said distinct nanostructured nonlamellar liquid crystalline material.

20. The particle or material of claim 19 wherein said liquid phase comprises at least one bioactive oil.

21. The particle or material of claim 19 wherein said distinct nanostructured nonlamellar liquid crystalline material is a reversed phase nonlamellar liquid crystalline material.

22. The particle or material of claim 19 wherein said distinct nanostructured nonlamellar liquid crystalline material comprises
a reversed hexagonal phase material,
a reversed bicontinuous cubic phase material,
a reversed discrete cubic phase material, or
a reversed intermediate phase material.

23. The particle or material of claim 19 wherein said distinct nanostructured nonlamellar liquid crystalline material is polymerized.

24. The particle or material of claim 19 further comprising a stabilizing layer exterior to said particle or material.

25. The particle or material of claim 24, wherein said stabilizing layer is selected from the group consisting of a charged moiety, a polymer, and a surfactant.

26. The particle or material of claim 19, wherein said particle or material further comprises a coating.

27. The particle or material of claim 26, wherein said coating further comprises an active agent.

28. The particle of claim 20 wherein said at least one bioactive oil is selected from the group consisting of santalwood, cedarwood, patchouli, peppermint, carrot see, cloves, ylang-ylang, fir needle, mugwort, oregano, Roman chamomile, eucalyptus, ginger, thuja, hyssop, and myrrh.

29. The particle or material of claim 19 wherein said particle or material is suspended in a earner.

30. The particle or material of claim 19 wherein said particle or material is pharmaceutically acceptable.

31. The particle or material of claim 30 wherein said particle or material is pharmaceutically acceptable for injection.

32. The particle or material of claim 30 wherein said particle or material is pharmaceutically acceptable for oral delivery.

33. The particle or material of claim 19, wherein said one or more pockets or droplets have a diameter of 50 nm or greater.

34. A particle or material comprising
a distinct nanostructured nonlamellar liquid crystalline material;
one or more pockets or droplets of a liquid phase embedded within said distinct nanostructured nonlamellar liquid crystalline material, said liquid phase being selected from the group consisting of an oil and a polar solvent; and
at least one active agent dissolved or dispersed in said liquid phase or in said distinct nanostructured nonlamellar liquid crystalline material.

35. The particle or material of claim 34 wherein said distinct nanostructured nonlamellar liquid crystalline material is a reversed phase nonlamellar liquid crystalline material.

36. The particle or material of claim 34 wherein said distinct nanostructured nonlamellar liquid crystalline material comprises
a reversed hexagonal phase material,
a reversed bicontinuous cubic phase material,
a reversed discrete cubic phase material, or
a reversed intermediate phase material.

37. The particle or material of claim 34 wherein said distinct nanostructured nonlamellar liquid crystalline material is polymerized.

38. The particle or material of claim 34 further comprising a stabilizing layer exterior to said particle or material.

39. The particle or material of claim 38, wherein said stabilizing layer is selected from the group consisting of a charged moiety, a polymer, and a surfactant.

40. The particle or material of claim 34, wherein said particle or material further comprises a coating.

41. The particle or material of claim 40, wherein said coating further comprises an active agent.

42. The particle or material of claim 34 wherein said liquid phase is an oil and said oil is selected from the group consisting of benzyl benzoate, estragole, eugenol, isoeugenol, linalool, and the essential oils of basil, bay, bois de rose (rosewood), carrot seed, clovebud, eucalyptus, ginger, grapefruit, hyssop, lemon, balsam of Peru, mugwort, myrrh gum, bitter orange, oregano, palmarosa, patchouly, peppermint, petitgrain, rosemary, santaiwood oil, spearmint, thuja (cedar leaf), thyme, vanilla, and ylang ylang (cananga).

43. The particle or material of claim 34 wherein said liquid phase is a polar solvent and said polar solvent is selected from the group consisting of water, glycerol, and N,N-dimethylacetamide.

44. The particle or material of claim 34 wherein said at least one active agent is selected from the group consisting of pigments, fillers, texturizing agents, opacifiers, non-wovens, chelating agents, polymerization catalysts, explosives, and propellants.

45. The particle or material of claim 44 wherein said active agent is a pigment.

46. The particle or material of claim 44 wherein said active agent is a polymerization catalyst.

47. The particle or material of claim 44 wherein said active agent is an explosive.

48. The particle or material of claim 34, wherein said active agent is a bioactive agent.

49. The particle or material of claim 48 wherein said bioactive agent is selected from the group consisting of targeting moieties, membrane proteins, absorption agents, fertilizer, pesticides, nucleic acids, antineoplastic agents, antibiotics, antimetabolites, proteins, hormones, hormone analogs, antineoplastic adjuncts, radiation sources, pheromones, growth regulators, herbicides, taste modifiers, vaccines, radionuclides, insecticides, proteins, and medicaments.

50. The particle or material of claim 49 wherein said bioactive agent is a protein.

51. The particle or material of claim 49 wherein said bioactive agent is a nucleic acid.

52. The particle or material of claim 49 wherein said active agent is a medicament.

53. The particle or material of claim 34 wherein said particle or material is pharmaceutically acceptable.

54. The particle or material of claim 53 wherein said particle or material is pharmaceutically acceptable for injection.

55. The particle or material of claim 53 wherein said particle or material is pharmaceutically acceptable for oral delivery.

56. The particle or material of claim 34, wherein said one or more pockets or droplets have a diameter of 50 nm or greater.

57. A composition comprising,
a carrier; and
a particle or material dispersed within said carrier, said particle or material comprising
a distinct nanostructured nonlamellar liquid crystalline material; and
one or more pockets or droplets of a liquid phase embedded within said distinct nanostructured nonlamellar liquid crystalline material, said liquid phase being selected from the group consisting of an oil and a polar solvent.

58. The composition of claim 57 wherein said distinct nanostructured nonlamellar liquid crystalline material is a reversed phase nonlamellar liquid crystalline material.

59. The composition of claim 57 wherein said distinct nanostructured nonlamellar liquid crystalline material comprises a reversed hexagonal phase material,
a reversed bicontinuous cubic phase material,
a reversed discrete cubic phase material, or
a reversed intermediate phase material.

60. The composition of claim 57 wherein said distinct nanostructured nonlamellar liquid crystalline material is polymerized.

61. The composition of claim 57 wherein said composition further includes a stabilizing layer on an exterior surface of said particle or material.

62. The composition of claim 61, wherein said stabilizing layer is selected from the group consisting of a charged moiety, a polymer, and a surfactant.

63. The composition of claim 57, wherein said particle or material further comprises a coating.

64. The particle or material of claim 63, wherein said coating further comprises an active agent.

65. The composition of claim 57 wherein said liquid phase is an oil and said oil is selected from the group consisting of benzyl benzoate, estragole, eugenol, isoeugenol, linalool, and the essential oils of basil, bay, bois de rose (rosewood), carrot seed, clovebud, eucalyptus, ginger, grapefruit, hyssop, lemon, balsam of Peru, mugwort, myrrh gum, bitter orange, oregano, palmarosa, patchouly, peppermint, petitgrain, rosemary, santalwood oil, spearmint, thuja (cedar leaf), thyme, vanilla, and ylang ylang (cananga).

66. The composition of claim 57 wherein said liquid phase is a polar solvent and said polar solvent is selected from the group consisting of water, glycerol, and N,N-dimethylacetamide.

67. The composition of claim 57 further comprising at least one active agent dissolved or dispersed in said liquid phase or in said distinct nanostructured nonlamellar liquid crystalline material.

68. The composition of claim 67 wherein said at least one active agent is selected from the group consisting of pigments, fillers, texturizing agents, opacifiers, non-wovens, chelating agents, polymerization catalysts, explosives, and propellants.

69. The composition of claim 68 wherein said active agent is a pigment.

70. The composition of claim 68 wherein said active agent is a polymerization catalyst.

71. The composition of claim 68 wherein said active agent is an explosive.

72. The composition of claim 67 wherein said active agent is a bioactive agent.

73. The composition of claim 72 wherein said bioactive agent is selected from the group consisting of targeting moieties, membrane proteins, absorption agents, fertilizer, pesticides, nucleic acids, antineoplastic agents, antibiotics, antimetabolites, proteins, hormones, hormone analogs, antineoplastic adjuncts, radiation sources, pheromones, growth regulators, herbicides, taste modifiers, vaccines, radionuclides, insecticides, proteins, and medicaments.

74. The composition of claim 73 wherein said active agent is a protein.

75. The composition of claim 73 wherein said active agent is a nucleic acid.

76. The composition of claim 73 wherein said active agent is a medicament.

77. The composition of claim 57 wherein said composition is pharmaceutically acceptable.

78. The composition of claim 77 wherein said composition is pharmaceutically acceptable for injection.

79. The composition of claim 77 wherein said composition is pharmaceutically acceptable for oral delivery.

80. The composition of claim 57, wherein said liquid phase is an oil and said carrier is hydrophobic.

81. The composition of claim 57, wherein said liquid phase is a polar solvent and said carrier is hydrophobic.

82. The composition of claim 57, wherein said liquid phase is an oil and said carrier is hydrophilic.

83. The composition of claim 57, wherein said liquid phase is a polar solvent and said carrier is hydrophilic.

84. The particle or material of claim 57, wherein said one or more pockets or droplets have a diameter of 50 nm or greater.

* * * * *